United States Patent [19]
Bru-Magniez et al.

[11] Patent Number: 5,389,632
[45] Date of Patent: Feb. 14, 1995

[54] PYRAZOLOPYRIMIDINE DERIVATIVES WHICH ARE ANGIOTENSIN II RECEPTOR ANTAGONISTS

[75] Inventors: Nicole Bru-Magniez, Paris; Timur Güngör, Rueil Malmaison; Jean-Marie Teulon, La Celle Saint Cloud, all of France

[73] Assignee: Laboratoires UPSA, Agen, France

[21] Appl. No.: 21,897

[22] Filed: Feb. 24, 1993

Related U.S. Application Data

[63] Continuation-in-part of Ser. No. 863,955, Apr. 6, 1992, Pat. No. 5,231,094.

[30] Foreign Application Priority Data

| Feb. 24, 1992 | [FR] | France | 92 02109 |
| Apr. 30, 1992 | [FR] | France | 92 05417 |
| Feb. 18, 1993 | [WO] | WIPO | PCT/FR93/00160 |

[51] Int. Cl.⁶ .......................... C07D 487/04
[52] U.S. Cl. .................. 514/233.2; 514/258; 544/117; 544/281
[58] Field of Search .................. 544/117, 281; 514/233.2, 258

[56] References Cited

U.S. PATENT DOCUMENTS

| 5,055,472 | 10/1991 | Fujikawa | 514/258 |
| 5,217,973 | 8/1993 | Bru-Magniez et al. | 544/118 |
| 5,250,521 | 10/1993 | Allen et al. | 514/83 |

FOREIGN PATENT DOCUMENTS

93-17024 9/1993 WIPO .

*Primary Examiner*—Donald G. Daus
*Attorney, Agent, or Firm*—Rosen, Dainow & Jacobs

[57] ABSTRACT

The present invention relates to the derivatives of the formula

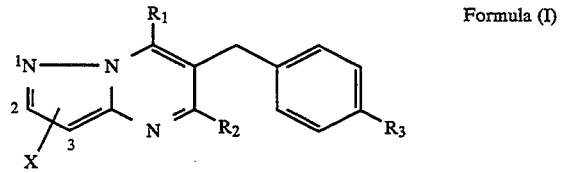

Formula (I)

and their tautomeric forms, as well as their addition salts, and to their use in therapeutics, especially for the treatment and prevention of cardiovascular diseases and in particular for the treatment of hypertension, cardiac insufficiency and diseases of the arterial wall, especially atherosclerosis.

17 Claims, No Drawings

PYRAZOLOPYRIMIDINE DERIVATIVES WHICH ARE ANGIOTENSIN II RECEPTOR ANTAGONISTS

This application is a continuation-in-part of U.S. application Ser. No. 07/863,955, filed Apr. 6, 1992, now U.S. Pat. No. 5,231,094.

The present invention relates, by way of novel products, to the pyrazolopyrimidine derivatives of general formula (I) below and their tautomeric forms and, where appropriate, their addition salts, in particular the pharmaceutically acceptable addition salts.

The compounds in question have a very valuable pharmacological profile insofar as they possess antagonistic properties towards the angiotensin II receptors, and antiproliferative properties. They are therefore particularly indicated for the treatment and prevention of cardiovascular diseases and in particular for the treatment of hypertension, for the treatment of cardiac insufficiency and for the treatment and prevention of diseases of the arterial wall, especially atherosclerosis.

The present invention further relates to the method of preparing said products and to their uses in therapeutics.

These pyrazolopyrimidine derivatives and their tautomeric forms have general formula (I):

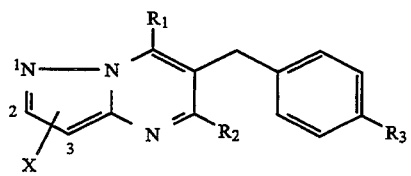

Formula (I)

In formula (I):
one of the radicals $R_1$ and $R_2$ is
 a lower alkyl radical having 1 to 6 carbon atoms; or
 an ether radical of the formula $-(CH_2)_pOR$, in which p is an integer from 1 to 6 and R is a lower alkyl radical having 1 to 6 carbon atoms or a benzyl radical; and
the other radical $R_1$ or $R_2$ is
 the hydrogen atom;
 a halogen atom;
 a lower alkyl radical having 1 to 6 carbon atoms; or
 a radical selected from the group comprising the radicals $OR_4$, $SR_4$, $NR_5R_6$ and $NH(CH_2)_n-NR_5R_6$,
in which:
 $R_4$ is
  the hydrogen atom;
  a lower alkyl radical having 1 to 6 carbon atoms or a $C_3-C_7$-cycloalkyl radical;
  a radical $(CH_2)_m-COOR'$, m being an integer from 1 to 4 and R' being the hydrogen atom or a lower alkyl radical having 1 to 6 carbon atoms; or
  a radical $(CH_2)_m-O-R'$, m and R' being as defined above;
 $R_5$ and $R_6$, which are identical or different, are
  the hydrogen atom; or
  a lower alkyl radical having 1 to 6 carbon atoms or a $C_3-C_7$-cycloalkyl radical; or
 $R_5$ and $R_6$, taken together with the nitrogen atom to which they are attached, form a heterocycle selected from morpholine, pyrrolidine or piperidine; and n is an integer from 1 to 4;
X, in the 2- or 3-position of the pyrazolo[1,5-a]-pyrimidine ring, is
 the hydrogen atom;
 a lower alkyl radical having 1 to 6 carbon atoms; or
 a radical selected from the group comprising the hydroxyl radical and the radical $COOR'$, R' being as defined above; and
$R_3$ is a radical of the formula

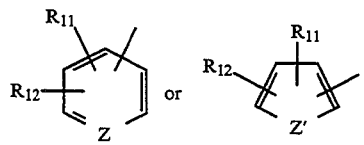

in which:
 Z is CH or N or Z' is S or O;
 $R_{11}$ is the hydrogen atom or a halogen atom; and
 $R_{12}$ is a tetrazole radical, CN, COOH or $CONH_2$.

Advantageously, the derivatives according to the invention are the derivatives of formula (I) given above in which:
one of the radicals $R_1$ and $R_2$ is
 a lower alkyl radical having 1 to 6 carbon atoms; and
the other radical $R_1$ or $R_2$ is
 the hydrogen atom;
 a halogen atom;
 a lower alkyl radical having 1 to 6 carbon atoms; or
 a radical selected from the group comprising the radicals OH, $NR_5R_6$ and $NH(CH_2)_n-NR_5R_6$,
in which:
 $R_5$ and $R_6$, which are identical or different, are
  the hydrogen atom; or
  a lower alkyl radical having 1 to 6 carbon atoms; or
 $R_5$ and $R_6$, taken together with the nitrogen atom to which they are attached, form a heterocycle selected from morpholine or pyrrolidine; and
 n is an integer from 2 to 4;
X, in the 2- or 3-position of the pyrazolo[1,5-a]-pyrimidine ring, is
 the hydrogen atom; or
 a lower alkyl radical having 1 to 6 carbon atoms; and
$R_3$ is one of the following radicals:

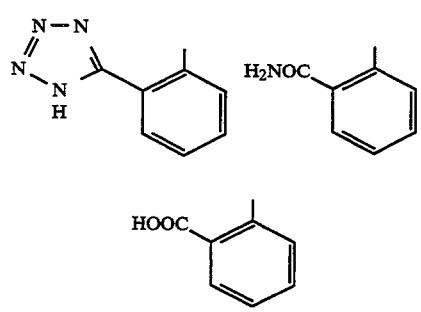

The above-mentioned derivatives of formula (I) must also be considered in their tautomeric form.

The above-mentioned derivatives of formula (I) can take the form of addition salts, in particular the pharmaceutically acceptable addition salts.

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$–$C_7$-Cycloalkyl radical is understood as meaning a saturated cyclic hydrocarbon radical, preferably a cyclopropyl, cyclobutyl, cyclohexyl or cycloheptyl radical.

Halogen is understood as meaning a chlorine, bromine, iodine or fluorine atom.

In one embodiment, $R_1$ is an n-propyl group.

In another embodiment, $R_1$ is a hydroxyl group.

In another embodiment, $R_1$ is a morpholinoethylamino group.

In another embodiment, $R_1$ is an amino group.

In another embodiment, $R_1$ is a diethylamino group.

In one embodiment, $R_2$ is a hydroxyl group.

In another embodiment, $R_2$ is an n-propyl group.

In one embodiment, X is the hydrogen atom.

In one embodiment, $R_3$ is a 2-(1H-tetrazol-5-yl)phenyl group.

The particularly preferred compounds of the invention are selected from the products of the formulae

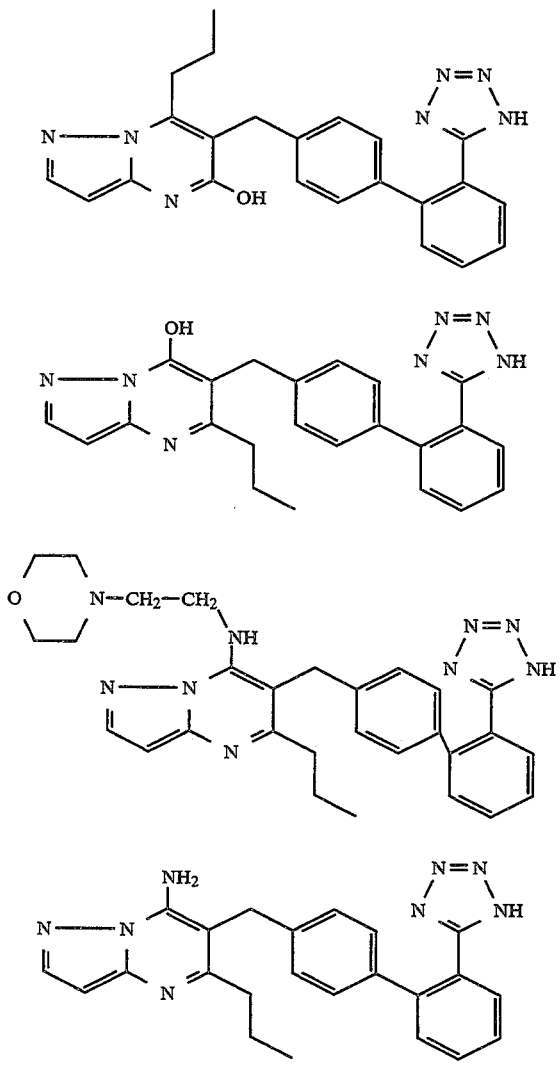

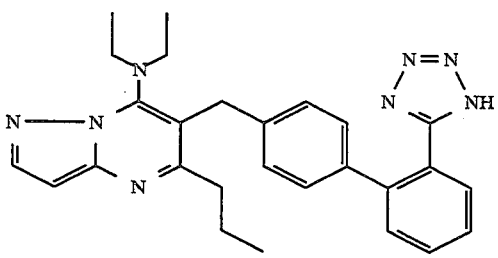

In general terms, the method of preparing the compounds of formula (I) comprises:

a) preparing a compound of formula ($\alpha$):

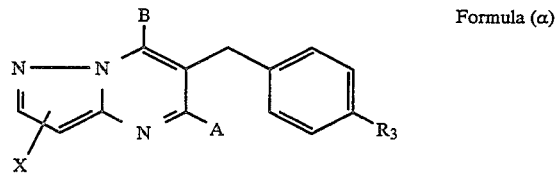

Formula ($\alpha$)

in which:

X and $R_3$ are as defined above; and

A and B are in one case a hydroxyl group or a lower alkyl radical having 1 to 6 carbon atoms and in the other case a lower alkyl radical having 1 to 6 carbon atoms or an ether radical of the formula —$(CH_2)_p$—OR, in which p is an integer from 1 to 6 and R is a lower alkyl radical having 1 to 6 carbon atoms or a benzyl radical, by condensing a 3-aminopyrazole of formula (II):

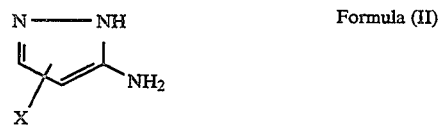

Formula (II)

in which X is as defined above, with a derivative of formula ($\beta$):

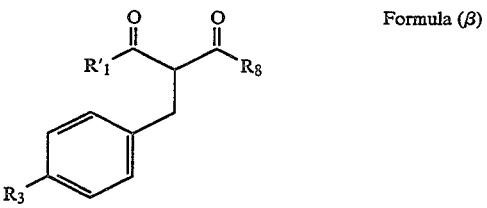

Formula ($\beta$)

in which $R'_1$ is a lower alkyl radical having 1 to 6 carbon atoms or an ether radical of the formula —$(CH_2)_p$—OR, in which p is an integer from 1 to 6 and R is a lower alkyl radical having 1 to 6 carbon atoms or a benzyl radical, $R_8$ is a lower alkyl radical having 1 to 6 carbon atoms or a lower O-alkyl group having 1 to 6 carbon atoms, preferably methyl or ethyl, and $R_3$ is as defined above, in an aprotic solvent such as dichloro- or trichlorobenzene, or in an acid solvent such as acetic acid, or else in an alcohol in the presence of the corresponding sodium or potassium alcoholate, or else in pyridine or 2-methyl-5-ethylpyridine in the presence or absence of 4-dimethylaminopyridine, at a temperature of between 50° and 200° C.;

b) if appropriate, protecting the group carried by R$_3$ using a method known per se;

c) heating the derivative thus obtained from the derivative of formula (β), when the latter is a ketoester, in an appropriate reagent such as, for example, POCl$_3$, to convert the hydroxyl group represented by A or B to a chlorine atom;

d) heating this chlorinated derivative in the presence of a nucleophile containing nitrogen, oxygen or sulfur, under reflux in an alcohol or in an autoclave at 100° C., in the presence or absence of a base such as, for example, Na$_2$CO$_3$, to give a derivative of formula (α) in which A and B have the same meanings as R$_1$ and R$_2$ respectively;

e) if appropriate, deprotecting the group carried by R$_3$;

e$_1$) converting this group to an acid group, for example by hydrolysis in the case where this group is a nitrile; or e$_2$) converting this group to a tetrazole group, for example, in the case where this group is a nitrile, by reaction with a trialkyltin azide with heating in toluene or xylene, followed by a treatment with gaseous hydrochloric acid in tetrahydrofuran; or e$_3$) converting this group to an amide group, for example, in the case where this group is a nitrile, by reaction with sulfuric acid, or by reaction with hydrogen peroxide, or else by reaction with polyphosphoric acid; and f) if appropriate, converting the resulting derivative to an addition salt, preferably a pharmaceutically acceptable addition salt.

According to the invention, it will be possible to synthesize the compounds of formula (I) in accordance with the following reaction sequence:

Methods known per se, such as, for example, the Claisen reaction or the method using Meldrum's acid, which methods can be found in the following literature references:

HAUSER C. R.; SWAMER F. W.; ADAMS J. T.; Org. Reaction, vol. VIII, 1954, 59–196, HENNE A. L.; TEDDER J. M.; J. Chem. Soc., 1953, 3628, BRESLOW D. S.; BAUMGARTEN E.; HAUSER C. R.; J. Am. Chem. Soc., 1944, 66, 1286, OIKAWA Y.; SUGANO K.; YONEMITSU O.; J. Org. Chem., 1978, 43(10), 2087–88, WIERENGA W.; SKULNICK H. I.; J. Org. Chem., 1979, 44, 310,

HOUGHTON R.; LAPHAM D.; SYNTHESIS, 1982, 6, 451-2,

BRAM G.; VILKAS M.; Bull. Soc. Chim. France, 1964(5), 945–51,

BALYAKINA M. V.; ZHDANOVICH E. S.; PREOBRAZHENSKII N. A.; Tr. Vses. Nauchn. Issled. Vitam in. Inst., 1961, 7, 8–16, RENARD M.; MAQUINAY A.; Bull. Soc. Chim. Belg., 1946, 55, 98–105, BRUCE F. W.; COOVER H. W.; J. Am. Chem. Soc., 1944, 66, 2092–94, and EBY C. J. and HAUSER C. R.; J. Am. Chem. Soc., 1957, 79, 723–5, will be used to prepare the compounds of formula (III):

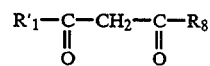  Formula (III)

in which R' is a lower alkyl radical having 1 to 6 carbon atoms or an ether radical of the formula —(CH$_2$)$_p$—OR, in which p is an integer from 1 to 6 and R is a lower alkyl radical having 1 to 6 carbon atoms or a benzyl radical, and R$_8$ is a lower alkyl radical having 1 to 6 carbon atoms or a lower O-alkyl group having 1 to 6 carbon atoms, preferably methyl or ethyl.

The compounds of the formula

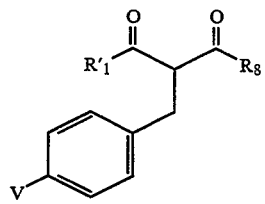  Formula (V)

will be obtained by benzylating the compounds of formula (III) with compounds of formula (IV):

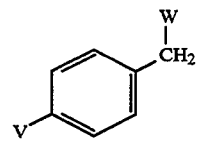  Formula (IV)

in the presence of a base such as sodium or potassium carbonate in acetone, a sodium or potassium alcoholate in an alcohol, or sodium or lithium hydride in solvents such as tetrahydrofuran, dioxane or dimethylformamide, for example, at a temperature of between 50° and 100° C., or else in the presence of one equivalent of lithium chloride or bromide and two equivalents of diisopropylethylamine in tetrahydrofuran under reflux, according to the following reference:

SUNG-EUN YOO; KYU YANG YI; Bull. Korean Chem. Soc., 1989, 10(1), 112.

These compounds of formula (V) can also be obtained by condensation of an aldehyde of formula (VI):

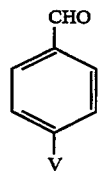  Formula (VI)

with the compounds of formula (III), followed by hydrogenation in the presence of a catalyst such as Raney nickel, palladium-on-charcoal or platinum oxide, in a solvent such as an alcohol or tetrahydrofuran, under pressure or at ordinary pressure if the substituents present allow it.

In more general terms, methods of preparing the compounds of formula (V) will be found in the following references:

DURGESHWARI P.; CHAUDHURY N. D.; J. Ind. Chem. Soc., 1962, 39, 735–6,

HEINZ P.; KREGLEWSKI A.; J. Prakt. Chem., 1963, 21(3–4), 186–197,

ZAUGG H. E.; DUNNIGAN D. A.; MICHAELS R. J.; SWETT L. R.; J. Org. Chem., 1961, 26, 644–51, KAGAN H. B.; HENG SUEN Y.; Bull. Soc. Chim. France, 1966(6), 1819–22, RATHKE M. W.; DEITCH J.; Tetrahedron Lett., 1971(31), 2953–6, BORRIES KUBEL; Liebigs Ann. Chem., 1980, 1392–1401, MARQUET J.; MORENO-MANAS M.; Chem. Lett., 1981, 2 173–6, IOFFE T.; POPOV E. M.; VATSURO K. V.; TULIKOVA E. K.; KABACHNIK M. I.; Tetrahedron, 1962, 18, 923–940, and SHEPHERD T. M.; Chem. Ind. (London), 1970, 17, 567.

In formula (IV), W is a halogen atom, preferably chlorine or bromine.

In the same formula:

V can be a group

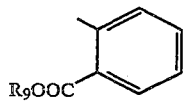

$R_9$ being a lower alkyl or benzyl radical, in which case the compounds of formula (IV) are prepared by reacting a magnesium compound of p-bromotoluene with a compound of the formula

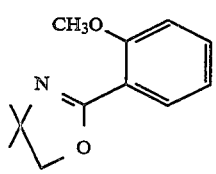

to give a compound of the formula

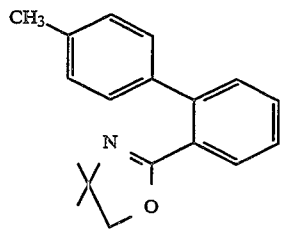

which is then hydrolyzed to give the compound of the formula

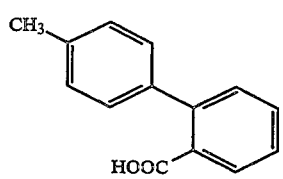

Procedures for the three steps described above will be found in the following reference:

MEYERS A. I.; MIHELICH E. D.; J. Am. Chem. Soc., 1975, 97, 7383.

The acid is then esterified with an alcohol of the formula $R_9OH$, $R_9$ being as defined above.

These derivatives are then brominated or chlorinated, for example with N-bromosuccinimide, N-chlorosuccinimide or bromine, in a solvent such as carbon tetrachloride, dibromoethane or dichloroethane, to give the compounds of formula (IV) in which V is the group

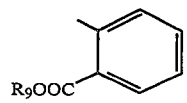

V can be the group

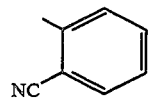

in which case the compound

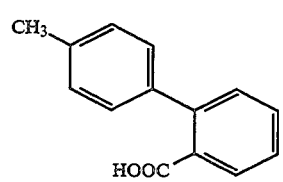

prepared above will be converted to the primary amide by reacting the acid chloride, obtained with thionyl chloride or phosphorus oxychloride, with aqueous ammonia, and this amide will be converted to the nitrile by reaction with phosphorus oxychloride in dimethylformamide or with thionyl chloride. Likewise, the compound

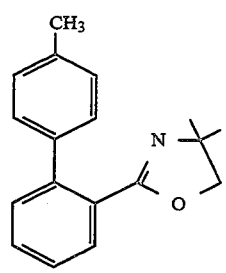

obtained above may be converted directly to the carbonitrile derivative by treatment in pyridine in the presence of $POCl_3$. The resulting nitrile derivative of the formula

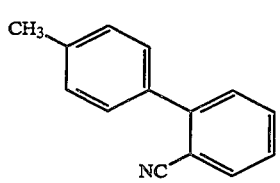

will then be brominated or chlorinated under the same conditions as the above ester to give the compounds of formula (IV) in which V is the group V can be a group

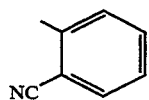

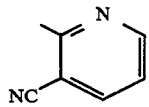

in which case the corresponding compounds of formula (IV) are synthesized in the following manner:

The magnesium compound

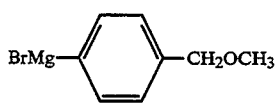

prepared by a conventional Grignard reaction, is converted to the zinc derivative by reaction with zinc chloride. This zinc derivative is condensed with 2-chloronicotinonitrile, in the presence of Ni(PΦ₃)Cl₂, to give the derivative of the formula

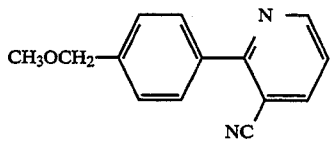

This compound, treated with boron tribromide in chloroform, will give the compounds of formula (IV) in which W is the bromine atom and V is the group

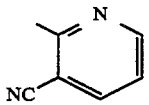

V can be a group

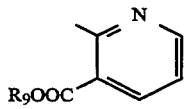

R₉ being as defined above, in which case the corresponding compounds of formula (IV) may be prepared from the nitrile prepared above of the formula

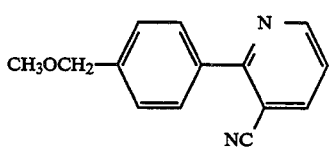

by conventional hydrolysis of the nitrile group followed by esterification of the acid obtained, or direct conversion of the nitrile group to the ester group by the methods known to those skilled in the art, followed by a treatment with boron tribromide in chloroform, to give the compounds of formula (IV) in which W is the bromine atom and V is the group

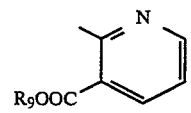

V can be a group

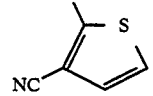

in which case the corresponding compounds of formula (IV) are synthesized in the following manner:

The compound of the formula

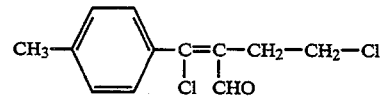

will be obtained from 4-chloro-4'-methylbutyrophenone of the formula

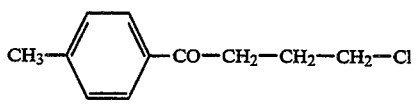

the preparation of which is described in Belgian patent 577,977 of 15th May 1959, CA: 54, 4629c, by treatment with phosphorus oxychloride and dimethylformamide under the conditions described in the following reference:

VOLODINA M. A.; TENENT'EV A. P.; KUDRYASHOVA V. A.; KABOSHINA L. N.; Khim. Geterosikl. Soedim; 1967, 5–8.

This compound is then treated with sodium sulfide in a solvent such as tetrahydrofuran, under reflux, to give the derivative

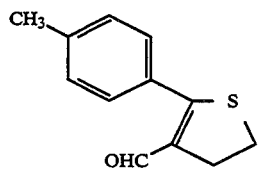

which is then converted in two steps to the nitrile derivative by dehydration of the oxime formed from the aldehyde and hydroxylamine. This dehydration may be carried out for example with acetic anhydride to give the nitrile compound

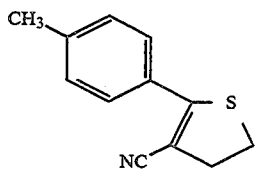

which may then be aromatized by treatment with bromine in carbon tetrachloride to give the compound

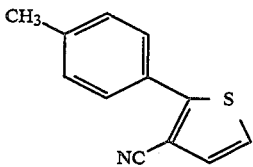

This compound can then be chlorinated or brominated with halogenating agents such as N-chlorosuccinimide or N-bromosuccinimide, in a solvent such as carbon tetrachloride or dibromoethane, to give the compounds of formula (IV) in which V is the group

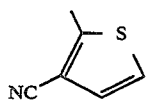

V can be a group

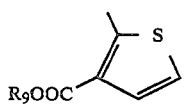

R$_9$ being as defined above, in which case the corresponding compounds of formula (IV) may be prepared from the nitrile prepared above of the formula

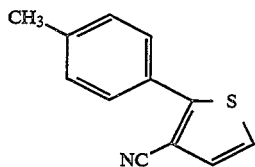

by conventional hydrolysis of the nitrile group followed by esterification of the acid obtained, or direct conversion of the nitrile group to the ester group by the methods known to those skilled in the art, followed by chlorination or bromination of the ester with N-chlorosuccinimide or N-bromosuccinimide, for example in carbon tetrachloride or dibromoethane, to give the compounds of formula (IV) in which W is the bromine atom or the chlorine atom and V is the group

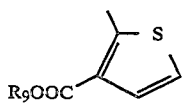

V can be a group

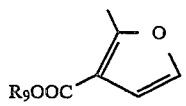

R$_9$ being as defined above, in which case the corresponding compounds of formula (IV) may be prepared by reacting the diazotized derivative of p-toluidine with 3-furoic acid to give the compounds of the formula

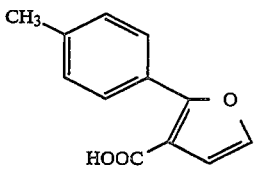

by the method described in the following literature reference:

A. JURASEK et al., Collect. Czech. Chem. Commun., 1989, 54, 215.

This compound will then be esterified by the conventional methods known to those skilled in the art to give the compound

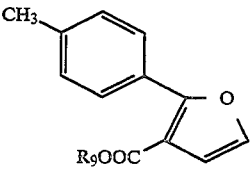

in which R$_9$ is as defined above, this derivative then being brominated or chlorinated by reaction with N-bromosuccinimide or N-chlorosuccinimide, for example in carbon tetrachloride or 1,2-dichloroethane, to give the derivative of formula (IV) in which W is the bromine atom or the chlorine atom and V is the group

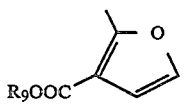

V can be a group

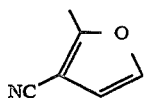

in which case the acid

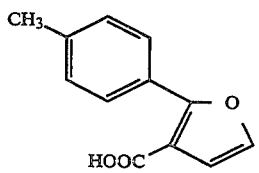

prepared above will be converted to the acid chloride by reaction with thionyl chloride and then to the amide by reaction with ammonia. The amide obtained will be converted to the nitrile by reaction with phosphorus oxychloride in dimethylformamide to give the compounds of the formula

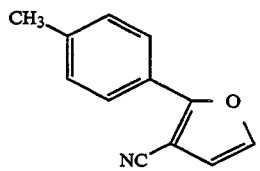

This derivative will then be brominated or chlorinated by reaction with N-bromosuccinimide or N-chlorosuccinimide, for example in carbon tetrachloride or 1,2-dichloroethane, to give the compounds of formula (IV) in which W is the bromine atom or the chlorine atom and V is the group

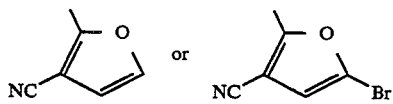

In formula (V), $R'_1$ and $R_8$ are as defined above and V is as defined in formula (IV).

However, the compounds of formula (V) in which V is a group

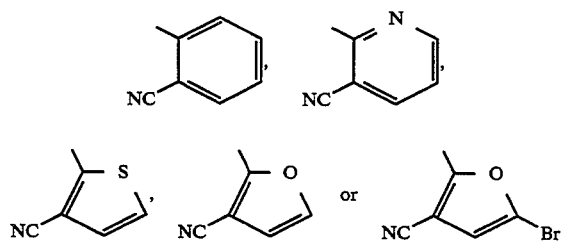

will react with one equivalent of sodium azide in a solvent such as dimethylformamide, in the presence of an ammonium salt such as ammonium chloride, or by heating in toluene or xylene with a trialkyltin azide, to give the compounds of formula (V) in which V is the group

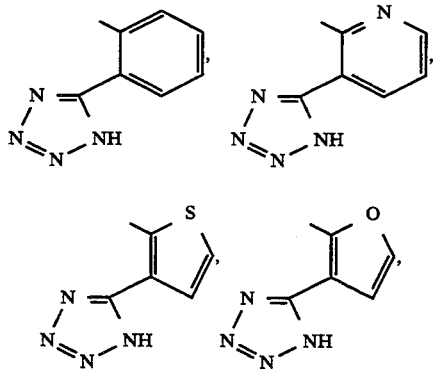

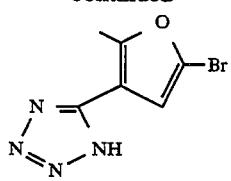

In formula (VI), V is as defined in formula (IV), but this condensation method will only be used when V possesses a group unaffected by hydrogenation.

Thus reaction of a 3-aminopyrazole of formula (II):

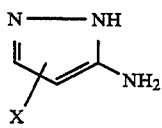

Formula (II)

in which X is as defined above—these products being commercially available or capable of being prepared by the methods known to those skilled in the art by reaction of hydrazine hydrate with a ketoacetonitrile of the formula X—CO—CH$_2$—CN, in which X is as defined above, or by other methods described in the following literature reference: Comprehensive Heterocyclic Chemistry, Pergamon Press, volume 5, pages 280 and 281—with the compounds of formula (V) in which $R'_1$ and $R_8$ are as defined above and V is one of the following groups:

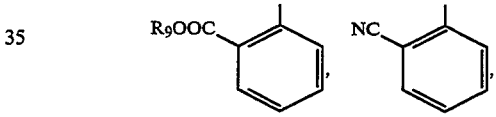

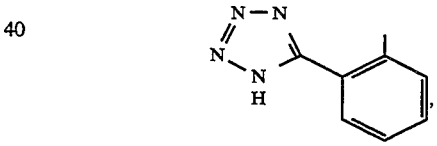

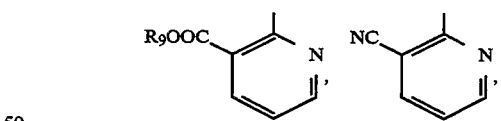

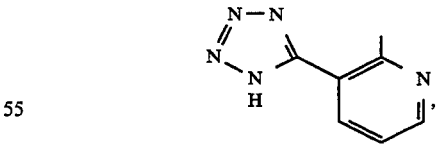

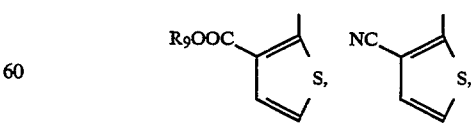

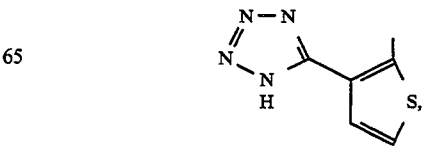

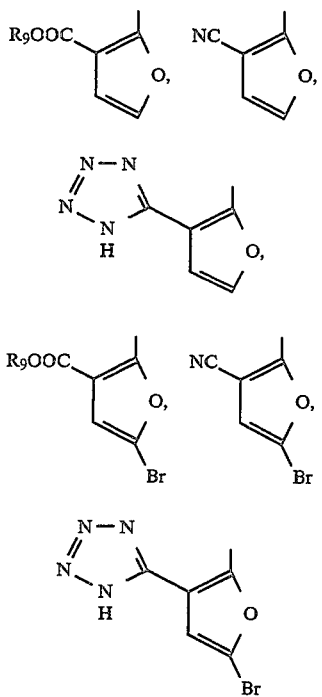

where R<sub>9</sub> is as defined above, will give the compounds of formulae (VIIa) and/or (VIIb):

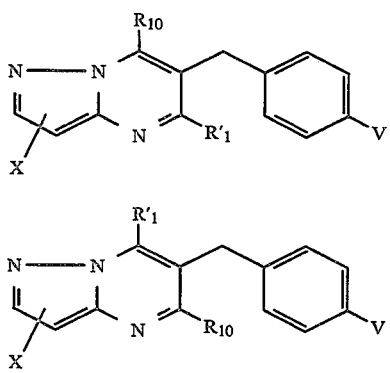

Formula (VIIa)

Formula (VIIb)

and their tautomeric forms, in which R′<sub>1</sub>, X and V are as defined above and R<sub>10</sub> is the hydroxyl group when the compounds of formula (V) are β-ketoesters and a lower alkyl radical having 1 to 6 carbon atoms in the case where these same compounds of formula (V) are β-diketones, by condensation in an aprotic solvent such as dichloro- or trichloro-benzene, or in an acid solvent such as acetic acid, or else in an alcohol in the presence of the corresponding sodium or potassium alcoholate, or else in pyridine or 2-methyl-5-ethylpyridine in the presence or absence of 4-dimethylaminopyridine, at a temperature of between 50° and 200° C.

In the case where V possesses a tetrazole group, the reaction temperatures should not exceed 140° C. so as not to decompose the tetrazole.

The reactions of aminopyrazoles or similar heteroaromatic amines with β-ketoesters and β-diketone derivatives are described well in the literature and, according to the operating conditions, the forms ob-tained are identified. Examples which may be cited are the studies by J. A. VAN ALLAN et al., J. Org. Chem., p. 779 to p. 801 (1959), and by L. A. WILLIAMS, J. Chem. Soc., p. 1829 (1960), and L. A. WILLIAMS, J. Chem. Soc., p. 3046 (1961).

Thus the compounds VIIa and VIIb will be identified for separate treatment.

The Applicant has discovered, however, that 2-methyl-5-ethylpyridine, in the presence or absence of 4-dimethylaminopyridine, is a preferred solvent for orientating the reaction towards the formation of the derivatives of formula (VIIb); in fact, the temperature (170°–180° C.) and the pH which are necessary for this orientation can be achieved using this solvent.

For example, if the derivatives of formulae (VIIa) and (VIIb) in which R<sub>10</sub> is a hydroxyl group are heated in POCl<sub>3</sub>, the derivatives of formulae (VIIIa) and (VIIIb):

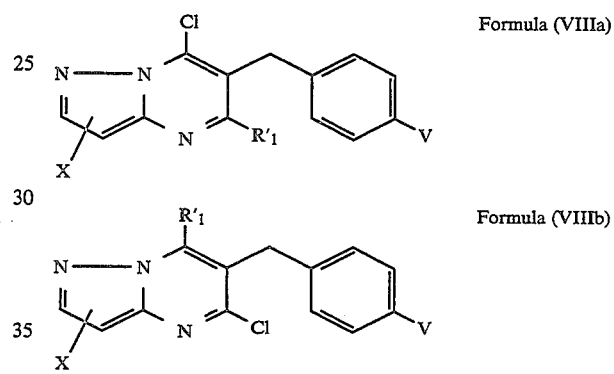

Formula (VIIIa)

Formula (VIIIb)

will be obtained, in which R′<sub>1</sub>, X and V are as defined above.

Hydrogenation of the derivatives of formulae (VIIIa) and (VIIIb), in the presence of a catalyst such as palladium-on-charcoal, will make it possible to replace the chlorine with a hydrogen atom, and the derivatives of formula (IX):

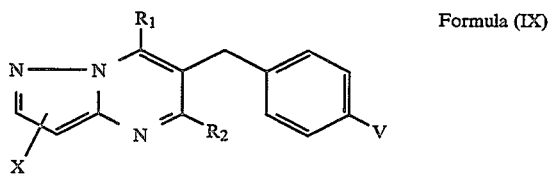

Formula (IX)

in which R<sub>1</sub>, R<sub>2</sub>, X and V are as defined above, will be obtained by heating the derivatives of formulae (VIIIa) and (VIIIb), in the presence of a nucleophile containing nitrogen, oxygen or sulfur, under reflux in an alcohol, in the presence or absence of a base such as Na<sub>2</sub>CO<sub>3</sub>, or in an autoclave at 100° C.

The compounds of formula (IX) in which V possesses an ester group COOR<sub>9</sub> may be hydrolyzed in an acid or basic medium, or hydrogenated in the case where R<sub>9</sub> is a benzyl, to give the compounds of formula (I) in which R′<sub>3</sub> possesses an acid group.

The compounds of formula (IX) in which V possesses a nitrile group will react with one equivalent of sodium azide in a solvent such as dimethylformamide, in the presence of an ammonium salt such as ammonium chloride, or by heating in toluene or xylene with a trialkyltin azide, for example trimethyltin or tributyltin azide, followed by an acid treatment, for example with gaseous hydrochloric acid in tetrahydrofuran, to give the compounds of general formula (I) in which $R_3$ possesses a tetrazol-5-yl group.

These same compounds in which V possesses a nitrile group may be converted by reaction with sulfuric acid, or by reaction with hydrogen peroxide, or else by reaction with polyphosphoric acid, to derivatives of general formula (I) in which $R_3$ possesses an amide group.

The derivatives in which V possesses a nitrile group or an amide group may also be converted by basic or acid hydrolysis to derivatives of general formula (I) in which $R_3$ possesses an acid group.

It is possible to obtain addition salts of some of the compounds of formula (I), especially pharmaceutically acceptable addition salts. In particular, when the compounds of formula (I) contain an acid or tetrazole group, there may be mentioned the salts of sodium, potassium, calcium, an amine such as dicyclohexylamine or an amino acid such as lysine. When they contain an amine group, there may be mentioned the salts of an inorganic or organic acid, such as, for example, the hydrochloride, methanesulfonate, acetate, maleate, succinate, fumarate, sulfate, lactate or citrate.

The novel compounds according to the invention possess remarkable pharmacological properties as angiotensin II receptor antagonists and antiproliferatives and can be used in therapeutics for the treatment and prevention of cardiovascular diseases and in particular for the treatment of hypertension, cardiac insufficiency and diseases of the arterial wall, especially atherosclerosis.

Thus the invention covers the pharmaceutical compositions which contain as the active principle the drugs consisting of a pharmaceutically effective amount of at least one compound of formula (I) as defined above, as well as one of its pharmaceutically acceptable addition salts where appropriate.

These compositions can be administered by the buccal, rectal, parenteral, transdermal or ocular route.

These compositions can be solid or liquid and can take the pharmaceutical forms commonly used in human medicine, such as, for example, simple or coated tablets, gelatin capsules, granules, suppositories, injectable preparations, transdermal systems and eye lotions. They are prepared by the customary methods. In said compositions, the active principle, consisting of a pharmaceutically effective amount of at least one compound of formula (I) as defined above, or one of its pharmaceutically acceptable addition salts, can be incorporated with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with antagonistic activity towards angiotensin II receptors, and/or antiproliferative activity, which permits especially a favorable treatment or prevention of cardiovascular diseases, in particular hypertension, cardiac insufficiency and diseases of the arterial wall, especially atherosclerosis, said composition comprising a pharmaceutically effective amount of at least one compound of formula (I) given above, or one of its pharmaceutically acceptable addition salts, which may be incorporated in a pharmaceutically acceptable excipient, vehicle or carrier.

The dosage varies especially according to the route of administration, the complaint treated and the subject in question.

For example, for an adult with an average weight of 60 to 70 kg, it can vary between 1 and 400 mg of active principle, administered orally in one or more daily doses, or from 0.01 to 50 mg, administered parenterally in one or more daily doses.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. This pharmaceutical composition can be formulated as gelatin capsules or tablets containing from 1 to 400 mg of active principle, or as injectable preparations containing from 0.01 to 50 mg of active principle.

The invention also covers a method of therapeutic treatment for mammals, which comprises administering to this mammal a therapeutically effective amount of at least one compound of formula (I) as defined above, or one of its pharmaceutically acceptable addition salts.

In animal therapeutics, the daily dose which can be used should normally be between 1 and 100 mg per kg.

Further characteristics and advantages of the invention will be understood more clearly from the following description of some Preparatory Examples, which in no way imply a limitation but are given by way of illustration.

EXAMPLE 1

Ethyl 3-oxohexanoate

Formula (III): $R'_1$=n-propyl, $R_8$=O-ethyl 176 g of 2,2-dimethyl-4,6-dioxo-1,3-dioxane (Meldrum's acid) are dissolved in 550 ml of dichloromethane and 188 ml of pyridine; the mixture is cooled to 5° C. with a bath of water and ice and 133 ml of butyryl chloride are added dropwise. When the addition is complete, the mixture is stirred for three hours at room temperature. The solution is washed with a dilute solution of hydrochloric acid, dried over magnesium sulfate and evaporated under vacuum to give an oil. This oil is dissolved in 700 ml of ethanol and the mixture is refluxed for six hours. The ethanol is evaporated off under vacuum and the residue obtained is distilled to give 145.4 g of ethyl 3-oxohexanoate in the form of an oil.

Boiling point (20 mm of mercury): 98°–100° C.

The compound of Example 2 was prepared by the procedure of Example 1.

EXAMPLE 2

Ethyl 3-oxoheptanoate

Formula (III): $R'_1$=n-butyl, $R_8$=O-ethyl

Boiling point (20 mm of mercury): 115°–120° C.

EXAMPLE 3

Ethyl 4-benzyloxy-3-oxobutanoate

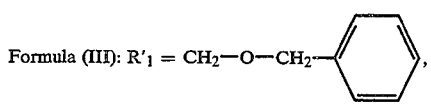

Formula (III): R'$_1$ = CH$_2$—O—CH$_2$—⟨phenyl⟩,

R$_8$ = O-ethyl 80 g of 60% NaH are added in portions to 800 ml of anhydrous THF. The medium is cooled to 10° C. and maintained at this temperature. 500 ml of benzyl alcohol are then introduced dropwise. A solution of 65.8 g of ethyl 4-chloroacetoacetate in 200 ml of benzyl alcohol is then added. The mixture is stirred at room temperature for 20 h. It is neutralized by the slow addition of acetic acid (120 ml) while being cooled with an ice bath. The whole is then poured into a mixture of water and ice and extracted with ether. The organic phase is washed with a solution of sodium bicarbonate, dried over MgSO$_4$ and then concentrated to give an orange oil. The product is purified by two successive distillations to give a yellow oil.

Boiling point (under 0.05 mm of mercury): 126°–132° C.

EXAMPLE 4

4'-Bromomethyl-2-cyanobiphenyl

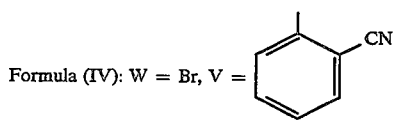

Formula (IV): W = Br, V = ⟨2-cyanophenyl⟩ a) Preparation of 2-cyano-4'-methylbiphenyl 563.8 g of (4'-methylbiphenyl-2-yl)carboxylic acid, prepared according to MEYERS A. I.; MIHELICH E. D.; J. Am. Chem. Soc., 1975, 97(25), 7383, are added in small portions to 800 ml of thionyl chloride. The mixture is refluxed for two hours. The thionyl chloride is concentrated under vacuum and the residue is poured into a 28% solution of ammonium hydroxide cooled beforehand with a bath of water and ice. The mixture is stirred for 30 minutes and the crystals obtained are filtered off, washed with water followed by ether and then dried to give 554.8 g of (4'-methylbiphenyl-2-yl)carboxamide in the form of crystals melting at 128°–132° C. These crystals are taken up in 1300 ml of thionyl chloride and the mixture is refluxed for 3 hours and then concentrated under vacuum to give an orange oil. This is taken up in two liters of chloroform and washed with water and the organic phase is then dried and concentrated to give 509.8 g of an oil, which crystallizes from pentane to give 467.3 g of 2-cyano-4'-methylbiphenyl.

Melting point: 46°–48° C.

b) 4'-Bromomethyl-2-cyanobiphenyl

The 467.3 g of 2-cyano-4'-methylbiphenyl prepared above are dissolved in 4.71 of 1,2-dichloroethane in the presence of 467.3 g of N-bromosuccinimide and 9.3 g of benzoyl peroxide. The mixture is heated very gradually so as to have good control over the exothermic effect. It is subsequently refluxed for 4 h, cooled to 50° C. and then washed 3 times with hot water and dried and the organic phase is concentrated to give cream-colored crystals.

Recrystallization from isopropanol gives 451 g of white crystals of 4'-bromomethyl-2-cyanobiphenyl.

Melting point: 128° C.

EXAMPLE 5

Ethyl 2-[(2'-cyanobiphenyl-4-yl)methyl]-3-oxohexanoate

Formula (V): R'$_1$ = n-propyl, R$_8$ = O-ethyl,

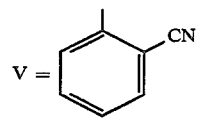

23 g of ethyl 3-oxohexanoate, prepared in Example 1, are dissolved in 120 ml of tetrahydrofuran. 30.3 g of 4'-bromomethyl-2-cyanobiphenyl, prepared in Example 4, and 4.7 g of lithium chloride are added and the mixture is stirred at room temperature. 39 ml of diisopropylethylamine are then introduced dropwise, causing a slight exothermic effect. The mixture is subsequently stirred for three hours at room temperature and then for ten hours under reflux. The solvents are evaporated off under vacuum and the residue is taken up in water and then extracted with chloroform. The organic phase is decanted and then washed with a dilute solution of hydrochloric acid, dried over magnesium sulfate and evaporated under vacuum to give 38 g of an orange oil.

Purification by chromatography on silica gel (eluent: CHCl$_3$) gives 32.3 g of ethyl 2-[(2'-cyanobiphenyl-4-yl)methyl]-3-oxohexanoate.

The compounds of Examples 6 to 10 are obtained by the procedure of Example 5 using the appropriate β-ketoester.

EXAMPLE 6

Ethyl 2-[(2'-cyanobiphenyl-4-yl)methyl]-3-oxoheptanoate

Formula (V): R'$_1$ = n-butyl, R$_8$ = O-ethyl,

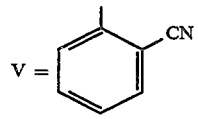

Oil used as such in the next step.

EXAMPLE 7

Ethyl 2-[(2'-cyanobiphenyl-4-yl)methyl]-3-oxobutanoate

Formula (V): R'$_1$ = methyl, R$_8$ = O-ethyl,

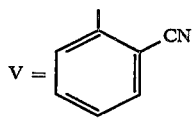

Yellow oil purified by chromatography on silica gel (eluent: chloroform 95%/ether 5%).

EXAMPLE 8

Ethyl 2-[(2'-cyanobiphenyl-4-yl)methyl]-3-oxopentanoate

Formula (V): R'₁ = ethyl, R₈ = O-ethyl,

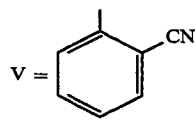

Oil purified by chromatography on silica gel (eluent: CHCl₃ 95%/ether 5%).

EXAMPLE 9

Ethyl 2-[(2'-cyanobiphenyl-4-yl)methyl]-4-methoxy-3-oxobutanoate

Formula (V): R'₁ = methoxymethyl, R₈ = O-ethyl,

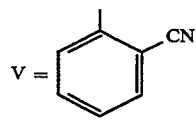

Yellow oil purified by chromatography on silica gel (eluent: CHCl₃ 95%/ether 5%).

EXAMPLE 10

Ethyl 4-benzyloxy-2-[(2'-cyanobiphenyl-4-yl)methyl]-3-oxobutanoate

Formula (V): R'₁ = CH₂—O—CH₂— ,

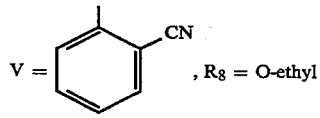 , R₈ = O-ethyl

Oil purified by chromatography twice in succession (eluents: chloroform, then cyclohexane 80%/ethyl acetate 20%).

EXAMPLE 11

Ethyl 2-[4-(3-cyano-2-pyridyl)benzyl]-3-oxohexanoate

Formula (V): R'₁ = CH₂—CH₂—CH₃,

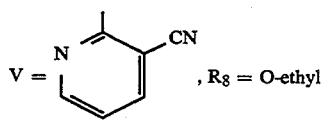 , R₈ = O-ethyl a) Preparation of 4-bromobenzyl methyl ether

A solution of sodium methylate, prepared from 11.8 g of sodium and 350 ml of methanol, is introduced dropwise into a suspension of 117.7 g of 4-bromobenzyl bromide in 350 ml of methanol. The mixture is stirred for 2 h at room temperature and left to stand overnight.

The methanol is evaporated off, the residue is taken up in ether and the organic phase is washed with water and then dried and concentrated to give a yellow oil, which is purified by distillation to give 102 g of bromobenzyl methyl ether as a colorless liquid.

Boiling point under 17 mm of mercury: 112°–114° C.

b) Synthesis of 3-cyano-2-(4-methoxymethylphenyl)-pyridine 2 g of the compound 4-bromobenzyl methyl ether, prepared above, are added to a suspension of 18 g of magnesium in 50 ml of anhydrous THF. The formation of the magnesium compound is initiated with a few crystals of iodine and, if necessary, by heating with a bath of warm water. A solution of 121.8 g of 4-bromobenzyl methyl ether in 200 ml of anhydrous THF is introduced dropwise so that the temperature does not exceed 40° C. The components are reacted for 1 h at room temperature and 800 ml of a solution of zinc chloride in ether are then introduced under excess nitrogen pressure. A white precipitate forms. The components are reacted for 1 h 30 min at room temperature. 800 mg of the coupling catalyst bis(triphenylphosphine)nickel-(II) chloride, [NiP(phenyl)₃]₂Cl₂, are added and a solution of 76.9 g of 2-chloronicotinonitrile in 300 ml of THF is then introduced. The mixture is stirred overnight at room temperature and concentrated under vacuum. The concentrate is taken up in a mixture of 1 l of dichloromethane, 1 l of water and 1 l of the disodium salt of EDTA. The emulsion is filtered on Célite 545. The organic phase is decanted, washed with water, dried and concentrated to give 133.6 g of an orange oil, which is purified by chromatography twice in succession (eluent: chloroform 95%/ether 5%). 69.4 g of 3-cyano-2-(4-methoxymethylphenyl)pyridine are thus isolated in the form of an orange oil, which crystallizes.

Melting point: 74° C.

c) Preparation of 3-cyano-2-(4-bromomethylphenyl)-pyridine

Formula (IV): W = Br, V = 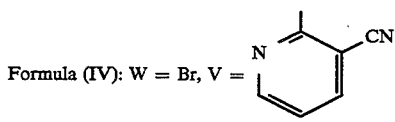

69.4 g of 3-cyano-2-(4-methoxymethylphenyl)pyridine, prepared in the previous step, are dissolved in 700 ml of chloroform stabilized with amylene. The solution is cooled to −10° C. A solution of 66 ml of BBr₃ in 200 ml of chloroform stabilized with amylene is introduced dropwise so that the temperature does not exceed 5° C. The mixture is left for 1 h 30 min in an ice bath. It is hydrolyzed with ice and then with water. It is filtered and the suspension is taken up in a mixture of water and chloroform. After decantation, the organic phases are combined, dried and then concentrated to give 78.2 g of cream-colored crystals of 3-cyano-2-(4-bromomethylphenyl)pyridine.

Melting point: 118° C.

d) Preparation of ethyl 2-[4-(3-cyano-2-pyridyl)benzyl]-3-oxohexanoate

Formula (V): R'₁ = CH₂—CH₂—CH₃, V = 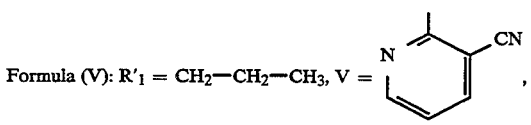 ,

-continued $R_8$ = O-ethyl

Following the procedure of Example 5, the expected derivative is obtained in the form of an orange oil, which is used as such in the next step.

EXAMPLE 12

Ethyl 2-[4-(3-cyano-2-thienyl)benzyl]-3-oxohexanoate

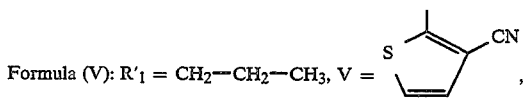

Formula (V): $R'_1$ = CH$_2$—CH$_2$—CH$_3$, V =

$R_8$ = O-ethyl a) Preparation of 4-chloro-1-(4-methylphenyl)butanone

A mixture of 560 ml of 4-chlorobutyryl chloride and 550 ml of toluene is added dropwise to a suspension of 740 g of AlCl$_3$ in 2 l of dichloromethane, the temperature being maintained at between 10° and 15° C. The reaction mixture is stirred for 30 min at room temperature and poured on to ice. After decantation, the organic phase is separated off and the aqueous phase is extracted with dichloromethane. The organic phases are combined, washed with water and then dried and concentrated under vacuum to give 994.5 g of 4-chloro-1-(4-methylphenyl)butanone in the form of an oil, which is used in the next step without further purification.

b) Preparation of 3-chloro-2-(2-chloroethyl)-3-(4-methylphenyl)prop-2-en-1-al 390 ml of POCl$_3$ are introduced dropwise, at a temperature of between 7° and 12° C., into a solution of 352.5 g of 4-chloro-1-(4-methylphenyl)butanone, prepared above according to Example 12 a), in 450 ml of DMF. The temperature is raised gradually, in the first instance to 50° C. over 2 h and then to 75° C. over 45 min. The mixture is poured on to ice and extracted three times with ether and the organic phases are combined, washed with water and then dried and evaporated to give 387.8 g of 3-chloro-2-(2-chloroethyl)-3-(4-methylphenyl)prop-2-en-1-al in the form of an oil, which is used as such in the next step.

c) Preparation of 4,5-dihydro-3-formyl-2-(4-methylphenyl)thiophene

A mixture of 200 g of 3-chloro-2-(2-chloroethyl)-3-(4-methylphenyl)prop-2-en-1-al, prepared in Example 12 b), 2.2l of THF, 276.5 g of Na$_2$S.9H$_2$O and 373 ml of water is refluxed for 6 h. It is concentrated under vacuum and the concentrate is taken up in water and extracted 3 times with ether. The organic phases are combined, washed with water, dried and concentrated to give 170.3 g of an oil, which crystallizes.

Melting point: below 50° C.

d) Preparation of 4,5-dihydro-3-formyl-2-(4-methylphenyl)thiophene oxime 132.1 g of hydroxylamine hydrochloride are added in portions to a solution of 323.5 g of the aldehyde prepared according to 12 c) in 800 ml of ethanol. A solution of sodium carbonate, prepared from 100.5 g of Na$_2$CO$_3$ and 700 ml of water, is then added dropwise. The mixture is heated at 40° C. for 5 min and the reaction is then left to proceed at room temperature for 1 h. The mixture is cooled to 15° C. and the solid is filtered off and washed with water and then with a mixture of isopropyl ether 50%/petroleum ether 50% to give 252 g of oxime. Extraction of the filtrate with dichloromethane gives a 2nd crop of 99 g of the expected oxime.

e) Preparation of 3-cyano-4,5-dihydro-2-(4-methylphenyl)thiophene

A solution of 171.8 g of the oxime prepared in Example 12 d) in 680 ml of acetic anhydride is refluxed for 3 h. It is concentrated to remove the excess anhydride and then distilled to give 115.3 g of nitrile derivative.

Boiling point under 0.05 mm of mercury: 140°–150° C.

f) Preparation of 3-cyano-2-(4-methylphenyl)thiophene 62 ml of bromine are introduced dropwise into a solution, preheated to 50° C., of 191.3 g of the nitrile prepared according to Example 12 e) in 1.85 l of CCl$_4$. The whole is refluxed until the evolution of HBr ceases. The CCl$_4$ is evaporated off and the residue is distilled to give 115.3 g of 3-cyano-2-(4-methylphenyl)thiophene.

Boiling point under 0.05–0.1 mm of mercury: 130°–150° C.

g) 2-(4-Bromomethylphenyl)-3-cyanothiophene

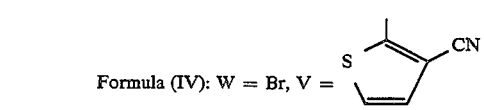

Formula (IV): W = Br, V =

182.2 g of the compound obtained in Example 12 f) are brominated according to Example 4 to give 133.7 g of 2-(4-bromomethylphenyl)-3-cyanothiophene.

Melting point: 80°–84° C.

h) Ethyl 2-[4-(3-cyano-2-thienyl)benzyl]-3-oxohexanoate

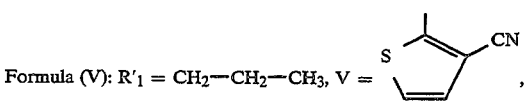

Formula (V): $R'_1$ = CH$_2$—CH$_2$—CH$_3$, V =

$R_8$ = O-ethyl

A mixture of 50 g of 2-(4-bromomethylphenyl)-3-cyanothiophene, prepared above, 40 g of ethyl 3-oxohexanoate, prepared in Example 1, 300 ml of THF, 62 ml of diisopropylethylamine and 15.6 g of LiBr is refluxed for 15 h. It is concentrated under vacuum, a dilute solution of hydrochloric acid is added and the mixture is extracted with ethyl acetate. The organic phases are combined, washed with water, dried and evaporated to give 62.4 g of ethyl 2-[4-(3-cyano-2-thienyl)benzyl]-3-oxohexanoate in the form of an oil, which is used without further purification.

EXAMPLE 13

Ethyl 2-[4-(3-cyano-2-furyl)benzyl]-3-oxohexanoate

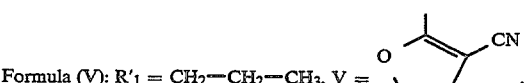

Formula (V): $R'_1$ = CH$_2$—CH$_2$—CH$_3$, V =

$R_8$ = O-ethyl a) Preparation of 2-(4-methylphenyl)-3-furanoic acid 70.7 g of p-toluidine, cooled with a bath of water and ice, are treated with 205 ml of 36% HCl. The mixture is then stirred at 55°–60° C. for 30 min before being cooled to 0° C. again. A solution of 45 g of NaNO₂ in 220 ml of water is then introduced. The mixture is stirred for 1 h at 0° C. This cold solution is introduced into a mixture of 49.3 g of 3-furanoic acid, 220 ml of acetone, 23.4 g of CuCl₂ and 6.3 g of water, cooled to −5° C. The whole is stirred at 0° C. for 2 h and then at room temperature for 48 h. It is extracted twice with ether and the organic phase is decanted, dried and concentrated to give an oil, which gives crystals when treated with water. The crystals are filtered off and washed with 50 ml of a 50% methanol/water mixture to give 13.4 g of 2-(4-methylphenyl)-3-furanoic acid.

Melting point: 166° C.

b) Preparation of 2-(4-methylphenyl)furan-3-carboxamide 20 ml of SOCl₂ are added to a solution of the 13.4 g of furanoic acid prepared above in 70 ml of toluene. The mixture is refluxed for 3 h and the excess SOCl₂ and the toluene are then distilled to give an oil, which is reacted at 5° C. with a solution of 100 ml of 1,2-dimethoxyethane saturated with ammonia. The precipitate is filtered off and washed with water and then with isopropyl alcohol to give 7 g of white crystals of amide.

Melting point: 174° C.

c) Preparation of 3-cyano-2-(4-methylphenyl)furan

A mixture of 12.2 g of the amide prepared above and 65 ml of SOCl₂ is refluxed for 3 h and concentrated under vacuum. The oil obtained is taken up in chloroform, and water and ice are then added. After decantation, the aqueous phase is extracted with chloroform and the organic phases are combined, dried and evaporated to give an oil. Purification by chromatography on silica gel (eluent: toluene) gives 7.5 g of an oil, which crystallizes.

Melting point: 66° C.

d) 2-(4-Bromomethylphenyl)-3-cyanofuran

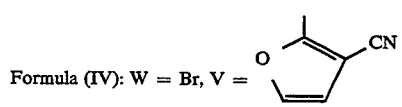

Formula (IV): W = Br, V =

The 7.5 g of compound obtained in Example 13 c) are brominated according to Example 4 to give, after purification by chromatography on silica gel (eluent: pentane 50%/toluene 50%), 4.6 g of 5-bromo-3-cyano-2-(4-methylphenyl)furan (melting point: 88° C.), 2.2 g of 5-bromo-3-cyano-2-(4-bromomethylphenyl)furan (melting point: 114° C.) and 2 g of 2-(4-bromomethylphenyl)-3-cyanofuran.

Melting point: 108° C.

The compound 5-bromo-3-cyano-2-(4-methylphenyl)furan is subjected to a further bromination reaction according to Example 4 to give 5-bromo-2-(4-bromomethylphenyl)-3-cyanofuran, which constitutes the compound of Example 13 d) bis.

e) Ethyl 2-[4-(3-cyano-2-furyl)benzyl]-3-oxohexanoate

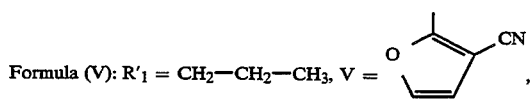

Formula (V): R′₁ = CH₂—CH₂—CH₃, V =

R₈ = O-ethyl

The resulting derivative 2-(4-bromomethylphenyl)-3-cyanofuran is treated according to Example 5 to give ethyl 2-[4-(3-cyano-2-furyl)benzyl]-3-oxohexanoate in the form of an oil, which is used in the crude state in the next step.

Likewise, the derivative 5-bromo-2-(4-bromomethylphenyl)-3-cyanofuran of Example 13 d) bis is treated according to Example 5 to give ethyl 2-[4-(5-bromo-3-cyano-2-furyl)benzyl]-3-oxohexanoate in the form of an oil, which constitutes the derivative of Example 13 bis.

EXAMPLE 14

3-[(2′-Cyanobiphenyl-4-yl)methyl]-2,4-dioxopentane

Formula (V): R′₁ = CH₃, R₈ = CH₃,

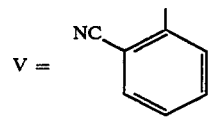

V =

32.8 g of 2,4-dioxopentane, 68 g of 4′-bromomethyl-2-cyanobiphenyl, prepared in Example 4, 88 ml of diisopropylamine and 10.6 g of anhydrous lithium chloride in 300 ml of tetrahydrofuran are refluxed for 27 h. The mixture is cooled and the precipitate is filtered off. The organic phase is concentrated to dryness to give 88.5 g of crystals. These are taken up in isopropanol and the mixture is filtered to isolate 38.8 g of unreacted 4′-bromomethyl-2-cyanobiphenyl. The concentrated mother liquors yield 26.5 g of an oil which, when purified on silica gel (eluent: chloroform), gives a further 5.3 g of 4′-bromomethyl-2-cyanobiphenyl and 12.2 g of the expected 3-[(2′-cyanobiphenyl-4-yl)methyl]-2,4-dioxopentane in the form of a yellow oil.

EXAMPLE 15

5-[(2′-Cyanobiphenyl-4-yl)methyl]-4,6-dioxononane

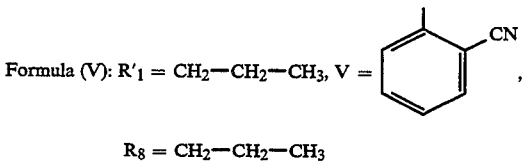

Formula (V): R′₁ = CH₂—CH₂—CH₃, V =

R₈ = CH₂—CH₂—CH₃

15.6 g of 4,6-dioxononane, prepared from methyl propyl ketone and ethyl butyrate in the presence of lithium amide (according to CA 42 : 4129 f), are dissolved in 160 ml of anhydrous DMF. 4 g of 60% NaH are added in portions. When the exothermic effect has subsided, the mixture is cooled to room temperature and a solution of 27.2 g of 4′-bromomethyl-2-cyanobiphenyl, prepared in Example 4, in 90 ml of DMF is introduced dropwise. The mixture is stirred for 30 min at room temperature and then heated at 60° C. for 2 h. It is concentrated under vacuum and the concentrate is taken up in a water/dichloromethane mixture and acidified with a dilute solution of HCl. After decantation, the aqueous phase is extracted twice with dichloromethane. The organic phases are washed with water, dried and then concentrated to give 36.3 g of an oil, which is purified by chromatography twice in succession (eluent: chloroform, then cyclohexane 90%/ethyl acetate 10% respectively) to give a solid identified by NMR as being the enol tautomer melting at 105° C., and an oil corresponding to the diketone tautomeric form.

EXAMPLE 16

2,4-Dioxo-3-[(2'-(1H-tetrazol-5-yl)biphenyl-4-yl)methyl]pentane

Formula (V): R'$_1$ = CH$_3$, R$_8$ = CH$_3$,

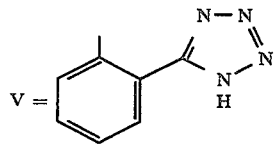

A mixture of 11.8 g of 3-[(2'-cyanobiphenyl-4-yl)methyl]-2,4-dioxopentane, prepared in Example 14, 200 ml of xylene and 9.3 g of trimethyltin azide is refluxed for 50 h. After 24 h, a second equivalent of trimethyltin azide is added.

The mixture is cooled and concentrated to give a viscous oil which, when chromatographed on silica gel (eluent: chloroform 90%/methanol 10%), gives 9.3 g of crystals.

An additional treatment with acetonitrile gives 6.2 g of analytically pure 2,4-dioxo-3-[(2'-(1H-tetrazol-5-yl)biphenyl-4-yl)methyl]pentane.

Empirical formula: C$_{19}$H$_{18}$N$_4$O$_2$. Melting point: 166° C.

EXAMPLE 17

Ethyl 2-[[2'-(1H-tetrazol-5-yl)biphenyl-4-yl]methyl]-3-oxohexanoate

Formula (V): R'$_1$ = n-propyl, R$_8$ = O-ethyl,

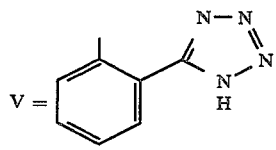

A mixture of 69.9 g of ethyl 2-[(2'-cyanobiphenyl-4-yl)methyl]-3-oxohexanoate, prepared according to Example 5, 700 ml of anhydrous toluene and 47.5 g of trimethyltin azide, prepared from sodium azide and trimethyltin chloride, is refluxed for 24 h. A further 47.5 g of trimethyltin azide are added and reflux is continued for 16 h. The mixture is concentrated to 50%. The orange solution obtained is purified by chromatography twice in succession (eluent: chloroform 90%/methanol 10%, then chloroform 95%/methanol 5%) to give 58 g of an orange oil, which crystallizes.

Melting point: 65° C.

EXAMPLE 18 (method A)

6-[(2'-Cyanobiphenyl-4-yl)methyl]-7-hydroxy-5-propylpyrazolo[1,5-a]pyrimidine

Formula (VIIa): R'$_1$ = n-propyl, X = H, R$_{10}$ = OH,

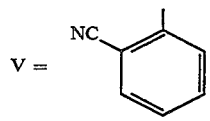

A mixture of 5 g of 3-aminopyrazole, 20.6 g of the β-ketoester of Example 5 and 90 ml of acetic acid is refluxed for 1 h 30 min. The precipitate obtained is filtered off and washed with ether and then with ethanol to give 12.7 g of 6-[(2'-cyanobiphenyl-4-yl)methyl]-7-hydroxy-5-propylpyrazolo[1,5-a]pyrimidine.

Melting point: 251° C. $^1$H NMR (DMSO-d$_6$): 2.65 (t, 2H, propyl CH$_2$); 3.96 (s, 2H, benzyl CH$_2$); 6.1 (d, 1H, H$_3$); 7.85 (d, 1H, H$_2$, J(H$_2$–H$_3$): 2Hz).

EXAMPLE 19 (method B)

6-[(2'-Cyanobiphenyl-4-yl)methyl]-5-hydroxy-7-propylpyrazolo[1,5-a]pyrimidine

Formula (VIIb): R'$_1$ = n-propyl, X = H, R$_{10}$ = OH,

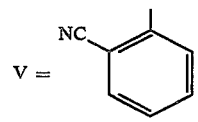

A mixture of 5 g of 3-aminopyrazole and 50 ml of 5-ethyl-2-methylpyridine is heated to 175° C. A solution of 21 g of the β-ketoester compound of Example 5 in 50 ml of 5-ethyl-2-methylpyridine is introduced dropwise.

The reaction mixture is heated for 6 h at 175° C. The precipitate of 11.9 g obtained is filtered off and identified as being the derivative of Example 18 described above.

The concentrated mother liquors are taken up in a mixture of water and chloroform. After decantation, the aqueous phase is extracted with chloroform and the organic phases are combined, dried and concentrated to give 10.7 g of amorphous crystals. Chromatography on silica gel (eluent: CHCl$_3$ 95%/methanol 5%) makes it possible to isolate 4.1 g of crystals of the compound 6-[(2'-cyanobiphenyl-4-yl)methyl]-5-hydroxy-7-propylpyrazolo[1,5-a]pyrimidine.

Melting point: 236° C. $^1$H NMR (DMSO-d$_6$): 2.99 (t, 2H, n-propyl CH$_2$); 3.95 (s, 2H, benzyl CH$_2$); 5.85 (d, 1H, H$_3$, J(H$_2$2 –H$_3$): 1.5 Hz); 7.75 (m, 2H, H$_2$ with an aromatic proton).

The following derivatives of Examples 20 to 26 were prepared by one of the two procedures of Examples 18 or 19 using the appropriate β-ketoester compounds described in Examples 5 to 15.

EXAMPLE 20

6-[( 2'-Cyanobiphenyl-4-yl )methyl]-7-hydroxy-2-methyl-5-propylpyrazolo[1,5-a]pyrimidine Formula (VIIa): R'$_1$ = n-propyl, X = 2-CH$_3$,

R$_{10}$ = OH,

V = 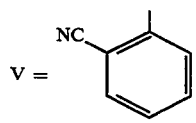

Melting point: 210° C. $^1$H NMR (DMSO-d$_6$): 2.3 (s, 3H, CH$_3$); 2.6 (t, 2H, propyl CH$_2$); 5.9 (s, 1H, H$_3$).

EXAMPLE 21

5-Butyl-6-[(2'-cyanobiphenyl-4-yl)methyl]-7-hydroxypyrazolo[1,5-a]pyrimidine

Formula (VIIa): R'$_1$ = n-butyl, X = H, R$_{10}$ = OH,

V = 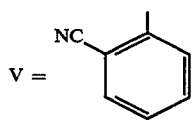

Melting point: 216° C. $^1$H NMR (CHCl$_3$): 2.8 (t, 2H, n-butyl CH$_2$); 4.07 (s, 2H, benzyl CH$_2$); 6.14 (d, 1H, H$_3$); 7.75 (d, 1H, H$_2$, J(H$_2$–H$_3$): 2.3 Hz).

EXAMPLE 22

6-[4-(3-Cyano-2-thienyl)benzyl]-7-hydroxy-5-propylpyrazolo[1,5-a]pyrimidine

Formula (VIIa): R'$_1$ = n-propyl, X = H, R$_{10}$ = OH,

V = 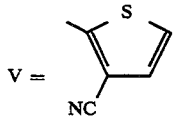

Melting point: 252° C. $^1$H NMR (DMSO-d$_6$): 2.64 (t, 2H, n-propyl CH$_2$); 3.96 (s, 2H, benzyl CH$_2$); 6.12 (d, 1H, H$_3$, J(H$_2$–H$_3$): 1.2 Hz).

EXAMPLE 23

6-[(2'-Cyanobiphenyl-4-yl)methyl]-5,7-dipropylpyrazolo[1,5-a]pyrimidine

Formula (VIIb): R'$_1$ = n-propyl, X = H, R$_{10}$ = n-propyl,

V = 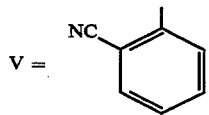

Melting point: 125° C. $^1$NMR (CHCl$_3$): 2.74 (t, 2H, n-propyl CH$_2$); 3.23 (q, 2H, n-propyl CH$_2$); 4.21 (s, 2H, benzyl CH$_2$); 6.61 (d, 1H, H$_3$); 8.09 (d, 1H, H$_2$, J(H$_2$–H$_3$): 2.2 Hz).

EXAMPLE 24

6-[4-(3-Cyano-2-pyridyl)benzyl]-7-hydroxy-5-propylpyrazolo[1,5-a]pyrimidine

Formula (VIIa): R'$_1$ = n-propyl, X = H,

R$_{10}$ = OH,

V = 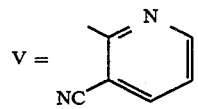

Melting point: 248° C. $^1$H NMR (DMSO-d$_6$): 2.65 (t, 2H, n-propyl CH$_2$); 3.99 (s, 2H, benzyl CH$_2$); 6.12 (d, 1H, H$_3$); 7.87 (d, 1H, H$_2$, J(H$_2$–H$_3$): 1.7 Hz).

EXAMPLE 25

Ethyl [6-[(2'-cyanobiphenyl-4-yl)methyl]-7-hydroxy-5-propylpyrazolo[1,5-a]pyrimidin-2-yl]carboxylate Formula (VIIa): R'$_1$ = n-propyl, X = 3-COOCH$_2$CH$_3$,

R$_{10}$ = OH,

V = 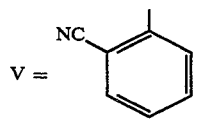

Melting point: 160° C. $^1$H NMR (DMSO-d$_6$): 2.83 (t, 2H, n-propyl CH$_2$); 3.99 (s, 2H, benzyl CH$_2$); 8.21 (s, 1H, H$_2$).

EXAMPLE 26

6-[(2'-Cyanobiphenyl-4-yl)methyl]-2,7-dihydroxy-5-propylpyrazolo[1,5-a]pyrimidine Formula (VIIa): R'$_1$ = n-propyl, X = 2-OH,

R$_{10}$ = OH,

V = 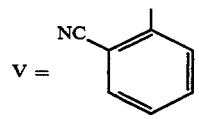

The following compounds will be obtained by reacting the β-ketoesters of Examples 9, 10, 13—13 bis and 14 with 3-aminopyrazole by one of the procedures of Examples 18 or 19:

6-[(2'-cyanobiphenyl-4-yl)methyl]-7-hydroxy-5-methoxymethylpyrazolo[1,5-a]pyrimidine
5-benzyloxymethyl-6-[(2'-cyanobiphenyl-4-yl)methyl]-7-hydroxypyrazolo[1,5-a]pyrimidine
6-[4-(3-cyano-2-furyl)benzyl]-7-hydroxy-5-propylpyrazolo[1,5-a]pyrimidine
6-[4-(5-bromo-3-cyano-2-furyl)benzyl]-7-hydroxy-5-propylpyrazolo[1,5-a]pyrimidine
6-[(2'-cyanobiphenyl-4-yl)methyl]-5,7-dimethylpyrazolo[1,5-a]pyrimidine

EXAMPLE 27

7-Chloro-6-[(2'-cyanobiphenyl-4-yl)methyl]-5-propylpyrazolo[1,5-a]pyrimidine

Formula (VIIIa): R'$_1$ = n-propyl, X = H,

V = 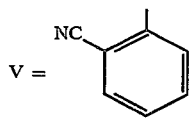

27 g of 6-[(2'-cyanobiphenyl-4-yl)methyl]-7-hydroxy-5-propylpyrazolo[1,5-a]pyrimidine, prepared in Example 18, are added in portions to 540 ml of POCl₃. The mixture is refluxed for 3 h. It is concentrated under vacuum. The oil obtained is taken up in dichloromethane and washed twice with a solution of water and ice. The organic phase is decanted, dried and concentrated. The yellow oil is taken up in ether to give 25.6 g of crystals of 7-chloro-6-[(2'-cyanobiphenyl-4-yl)methyl]-5-propylpyrazolo[1,5-a]pyrimidine.

Melting point: 137° C. ¹H NMR (CDCl₃): 2.8 (t, 2H, propyl CH₂); 6.7 (d, 1H, H₃); 8.2 (d, 1H, H₂, J(H₂-H₃): 2.2 Hz).

EXAMPLE 28

6-[(2'-Cyanobiphenyl-4-yl)methyl]-7-[2-(morpholin-4-yl)ethylamino]-5-propylpyrazolo[1,5-a]pyrimidine Formula (IX): R₁ = 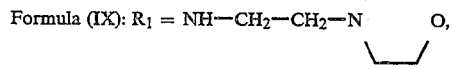

R₂ = n-propyl, X = H,

V = 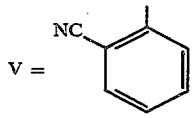

A mixture of 5 g of the chlorinated derivative prepared in Example 27, 1.8 g of 4-(2-aminoethyl)morpholine, 1.5 g of Na₂CO₃ and 100 ml of ethanol is refluxed for 7 h. A further 1.8 g of 4-(2-aminoethyl)morpholine are added and the mixture is refluxed for 8 h. It is concentrated under vacuum and taken up in a mixture of water and dichloromethane. The aqueous phase is decanted and extracted with dichloromethane. The organic phases are combined and dried. Evaporation of the solvent gives 5.9 g of a brown oil which is sufficiently pure for the next step.

¹H NMR (CDCl₃): 2.5 (t, 2H, propyl CH₂); 6.4 (d, 1H, H₃); 7.9 (d, 1H, H₂, J(H₂-H₃): 2.4 Hz).

EXAMPLE 29

6-[(2'-Cyanobiphenyl-4-yl)methyl]-7-methoxy-5-propylpyrazolo[1,5-a]pyrimidine

Formula (IX): R₁ = OCH₃, X = H, R₂ = n-propyl,

V = 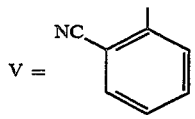

7.7 g of the chlorinated compound prepared in Example 27 are reacted at room temperature, for 6 h, with a solution of sodium methylate and 1,2-dimethoxyethane prepared from 0.6 g of sodium, 25 ml of methanol and 50 ml of 1,2-dimethoxyethane.

The reaction mixture is concentrated. The concentrate is taken up in a mixture of water and ethyl acetate. The precipitate obtained (1.4 g) is identified as 6-[(2'-cyanobiphenyl-4-yl)methyl]-7-hydroxy-5propyl-pyrazolo[1,5-a]pyrimidine, obtained in Example 18. The organic phase is chromatographed on silica gel (eluent: dichloromethane 90%/acetone 10%) to give 4 g of 6-[(2'-cyanobiphenyl-4-yl)methyl]-7-methoxy-5-propyl-pyrazolo[1,5-a]pyrimidine.

Melting point: 110° C. ¹H NMR (CDCl₃): 2.75 (q, 2H, propyl CH₂); 4.18 (s, 2H, benzyl CH₂); 4.29 (s, 3H, OCH₃); 6.60 (d, 1H, H₃); 8.07 (d, 1H, H₂, J(H₂-H₃): 2.3 Hz).

EXAMPLE 30

6-[(2'-Cyanobiphenyl-4-yl)methyl]-5-propyl-pyrazolo[1,5-a]pyrimidin-7-yl]2-methoxyethyl ether Formula (IX): R₁ = OCH₂CH₂OCH₃, X = H, R₂ = n-propyl, V = 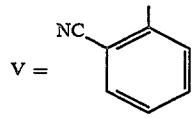

0.6 g of 60% NaH is added in portions to a mixture of 25 ml of 2-methoxyethanol and 50 ml of 1,2-dimethoxyethane. After 15 min, 5 g of the chlorinated compound prepared in Example 27 are introduced in portions, followed by 50 ml of 1,2-dimethoxyethane. The mixture is stirred for 3 h at room temperature and then for 3 h at 60° C. It is concentrated under vacuum and the concentrate is taken up in a mixture of water and ethyl acetate. After decantation, the aqueous phase is extracted with ethyl acetate. The combined organic phases are dried and evaporated to give 6.3 g of an oil, which is purified by chromatography on silica gel (eluent: dichloromethane 90%/acetone 10%) to give 4.2 g of 6-[(2'-cyanobiphenyl-4-yl)methyl]-5-propylpyrazolo[1,5-a]pyrimidin-7-yl]2-methoxyethyl ether.

Melting point: 106° C.

The compounds of Examples 31 to 34 were obtained by one of the procedures of Examples 28 to 30 using the appropriate nucleophiles.

EXAMPLE 31

6-[(2'-Cyanobiphenyl-4-yl)methyl]-7-(N-morpholino)-5-propylpyrazolo[1,5-a]-pyrimidine Formula (IX): R₁ = N-morpholino, R₂ = n-propyl, X = H, V = 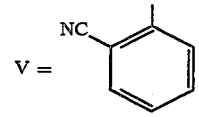

Melting point: 140° C. ¹H NMR (DMSO-d₆): 2.6 (t, 2H, propyl CH₂); 6.6 (d, 1H, H₃); 8.1 (d, 1H, H₂, J(H₂-H₃): 2.4 Hz).

EXAMPLE 32

6-[(2'-Cyanobiphenyl-4-yl)methyl]-5-propyl-7-[2-(pyrrolidin-1-yl)ethylamino]pyrazolo-[1,5-a]pyrimidine

Formula (IX): $R_1$ = NH—CH$_2$—CH$_2$—N $R_2$ = n-propyl, X = H,

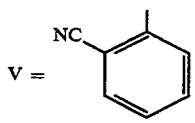

V =

Oil purified by chromatography on silica gel (eluent: CHCl$_3$ 90%/methanol 10%).

$^1$H NMR (CDCl$_3$): 2.6 (m, 4H, propyl CH$_2$+pyrrolidine CH$_2$); 6.4 (d, 1H, H$_3$, J(H$_2$–H$_3$): 2.1 Hz); 7.9 (d, 1H, H$_2$).

EXAMPLE 33

6-[(2'-Cyanobiphenyl-4-yl)methyl]-7-(piperidin-1-yl)-5-propylpyrazolo[1,5-a]-pyrimidine

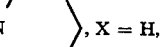

Formula (IX): $R_1$ = N , X = H, $R_2$ = n-propyl, V =

Crystallization from isopropyl ether.
Melting point: 118° C.

EXAMPLE 34

Ethyl [6-[(2'-cyanobiphenyl-4-yl)methyl]-5-propylpyrazolo[1,5-a]pyrimidin-7-yl]-mercaptoacetate

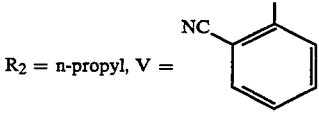

Formula (IX): $R_1$ = S—CH$_2$COOEt, X = H, $R_2$ = n-propyl, V =

Melting point: 126° C.

The compounds of Examples 35 and 36 were obtained by the procedure of Example 28, except that the reaction was carried out in an autoclave at 100° C. for 48 h.

EXAMPLE 35

6-[(2'-Cyanobiphenyl-4-yl)methyl]-7-N,N-diethylamino-5-propylpyrazolo[1,5-a]-pyrimidine

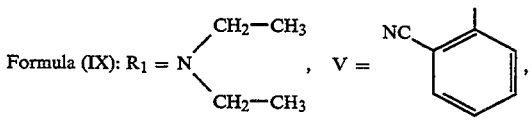

Formula (IX): $R_1$ = N(CH$_2$—CH$_3$)$_2$ , V =

$R_2$ = n-propyl, X = H

Oil purified by chromatography on silica gel (eluent: CH$_2$Cl$_2$ 95%/ethyl acetate 5%).

$^1$H NMR (DMSO-d$_6$): 2.6 (t, 2H, propyl CH$_2$); 6.6 (d, 1H, H$_3$, J(H$_2$–H$_3$): 2.1 Hz); 8.1 (d, 1H, H$_2$).

EXAMPLE 36

7-Amino-6-[(2'-cyanobiphenyl-4-yl)methyl]-5-propylpyrazolo[1,5-a]pyrimidine

Formula (IX): $R_1$ = NH$_2$, $R_2$ = n-propyl, X = H,

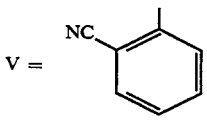

V =

Oil purified by chromatography on silica gel (eluent: CH$_2$Cl$_2$ 95%/acetone 5%). Crystallizes slowly.

Melting point: 158° C. $^1$H NMR (CDCl$_3$): 2.7 (t, 2H, propyl CH$_2$); 6.4 (d, 1H, H$_3$); 7.9 (d, 1H, H$_2$, J(H$_2$–H$_3$): 2 Hz).

EXAMPLE 37

6-[(2'-Cyanobiphenyl-4-yl)methyl]-5-propyl-pyrazolo[1,5-a]pyrimidine

Formula (IX): $R_1$ = H, X = H, $R_2$ = n-propyl,

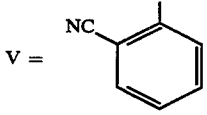

V =

A solution of 5.4 g of the chlorinated compound prepared in Example 27 in 110 ml of 2-methoxyethanol containing 1.2 g of anhydrous sodium acetate is hydrogenated, at atmospheric pressure and ambient temperature, in the presence of 1.4 g of 5% Pd-on-charcoal. The system is purged with nitrogen. The catalyst is filtered off on Célite 545 and washed with 2-methoxyethanol. The filtrate is concentrated and taken up in ether to give 5.2 g of crude product. Purification by chromatography on silica gel (eluent: dichloromethane 90%/acetone 10%) gives 4 g of 6-[(2'-cyanobiphenyl-4yl)methyl]-5-propylpyrazolo[1,5-a]pyrimidine.

Melting point: 154° C.

EXAMPLE 38

7-Hydroxy-5-propyl-6-[(2'-(1H-tetrazol-5-yl)biphenyl-4-yl)methyl]pyrazolo[1,5-a]pyrimidine Formula (I): $R_1$ = OH, $R_2$ = n-propyl, X= H, $R_3 =$ 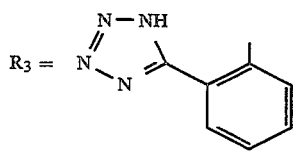

A mixture of 0.8 g of 3-aminopyrazole, 3.9 g of the β-ketoester of Example 17 and 25 ml of acetic acid is refluxed for 6 h. A further 0.4 g of aminopyrazole is added and the mixture is refluxed for a period of 6 h. It is concentrated under vacuum. The oil obtained is taken up in water to give 3.8 g of a solid, which is purified a first time by chromatography on silica gel (eluent: chloroform 80%/methanol 20% to remove the less polar products, then chloroform 70%/methanol 30% to elute the pyrazolopyrimidine compound). The resulting solid is treated with a normal solution of sodium hydroxide. The insoluble materials are removed and the clear solution is acidified to pH 4 by bubbling $SO_2$ to give a white precipitate. The compound is crystallized from ethanol to give 0.6 g of 7-hydroxy-5-propyl-6-[(2'-(1H-tetrazol-5-yl)biphenyl-4yl)methyl]pyrazolo[1,5-a]pyrimidine.

Empirical formula: $C_{23}H_{21}N_7O.2H_2O$. Melting point: $\geq 320°$ C. with decomposition. $^1H$ NMR (DMSO-$d_6$): 2.5 (m, 2H, propyl $CH_2$+DMSO-$d_6$); 6 (d, 1H, $H_3$); 7.8 (d, 1H, $H_2$, $J(H_2$-$H_3)$: 1.9 Hz).

EXAMPLE 39

5-Hydroxy-7-propyl-6-[(2'-(1H-tetrazol-5-yl)biphenyl-4-yl)methyl]pyrazolo[1,5-a]pyrimidine Formula (I): $R_1$ = n-propyl, X = H, $R_2$ = OH, $R_3 =$ 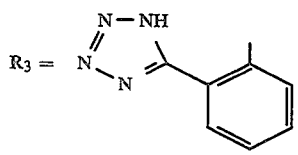

A mixture of 5 g of the derivative prepared in Example 19, 150 ml of xylene, 6 ml of DMF and 7 g of trimethyltin azide is heated at 115° C. for 50 h. The organic phase is decanted. The precipitate is taken up in THF. Gaseous hydrochloric acid is bubbled in until the precipitate dissolves.

The solution is concentrated under vacuum and the concentrate is taken up in water and triturated. The gum obtained is crystallized in the presence of acetonitrile. Recrystallization from isopropanol gives 0.7 g of 5-hydroxy-7-propyl-6-[(2'-(1H-tetrazol-5-yl)-biphenyl-4-yl)methyl]pyrazolo[1,5-a]pyrimidine.

Empirical formula: $C_{23}H_{21}N_7O$. Melting point: 260° C. $^1H$ NMR (DMSO-$d_6$): 2.93 (t, 2H, n-propyl $CH_2$); 3.86 (s, 2H, benzyl $CH_2$); 5.83 (d, 1H, $H_3$); 7.74 (d, 1H, $H_2$, $J(H_2$-$H_3)$: 1.9 Hz).

EXAMPLE 40

7-[(N-Morpholinoethyl)amino]-5-propyl-6-[(2'-(1H-tetrazol-5-yl)biphenyl-4-yl)methyl]pyrazolo[1,5-a]pyrimidine Formula (I): $R_1$ = 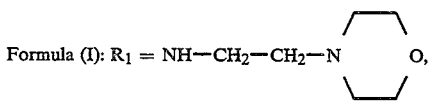

$R_2$ = n-propyl, X = H, $R_3 =$ 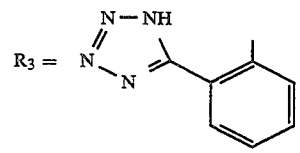

A mixture of 5.9 g of 6-[(2'-cyanobiphenyl-4-yl)methyl]-7-[2-(morpholin-4-yl)ethylamino]-5-propyl-pyrazolo[1,5-a]pyrimidine, prepared in Example 28, 3.1 g of trimethyltin azide and 120 ml of xylene is brought to the reflux point. After 15 h, a further 3.1 g of trimethyltin azide are added and the reflux reaction is continued for 20 h.

The thick oil is decanted from the xylene and taken up in THF. Acidification with gaseous hydrochloric acid gives a gummy precipitate, which is taken up in acetonitrile to give 4.7 g of a solid.

The base is freed by treatment with a solution of triethylamine/ethyl acetate. The compound is purified a first time by chromatography on silica gel (eluent: chloroform 80%/methanol 20%).

Recrystallization from ethanol gives 2.5 g of white crystals of 7-[(N-morpholinoethyl)amino]-5-propyl-6-[(2'-(1H-tetrazol-5-yl)biphenyl-4-yl)methyl]-pyrazolo[1,5-a]pyrimidine.

Empirical formula: $C_{29}H_{33}N_9O.0.1H_2O$. Melting point: 210° C. $^1H$ NMR (DMSO-$d_6$): 2.6 (t, 2H, propyl $CH_2$); 6.3 (d, 1H, $H_3$); S (d, 1H, $H_2$, $J(H_2$-$H_3)$: 2.2 Hz).

The following compounds of Examples 41 to 49 were prepared by any one of the methods described in Examples 38, 39 or 40.

EXAMPLE 41

7-Hydroxy-2-methyl-5-propyl-6-[(2'-(1H-tetrazol-5-yl)biphenyl-4-yl)methyl]-pyrazolo[1,5-a]pyrimidine hydrochloride Formula (I): $R_1$ = OH, $R_2$ = n-propyl, X = 2-$CH_3$, $R_3 =$ 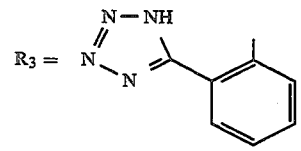

Empirical formula: $C_{24}H_{23}N_7O.HCl.0.2H_2O$. Melting point: 230°–232° C. with decomposition. $^1H$ NMR (DMSO-$d_6$): 2.6 (t, 2H, propyl $CH_2$); 6 (s, 1H, $H_3$).

EXAMPLE 42

7-Chloro-5-propyl-6-[(2'-(1H-tetrazol-5-yl)biphenyl-4-yl)methyl]pyrazolo[1,5-a]pyrimidine Formula (I): $R_1$ = Cl, $R_2$ = n-propyl, X = H,

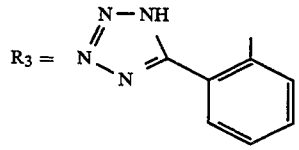

Empirical formula: $C_{23}H_{20}ClN_7$. Melting point: 234° C. $^1$H NMR (DMSO-$d_6$): 2.7 (t, 2H, propyl $CH_2$); 6.8 (d, 1H, $H_3$); 8.3 (d, 1H, $H_2$, J($H_2$–$H_3$): 2.3 Hz).

EXAMPLE 43 b 7-(N-Morpholino)-5-propyl-6-[(2'-(1H-tetrazol-5-yl)biphenyl-4-yl)methyl]pyrazolo[1,5-a]pyrimidine hydrochloride

$R_2$ = n-propyl, X = H,

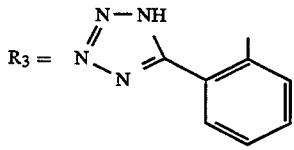

Empirical formula: $C_{27}H_{28}N_8O \cdot HCl$. Melting point: 210°–212° C. $^1$H NMR (DMSO-$d_6$): 2.8 (t, 2H, propyl $CH_2$); 6.6 (d, 1H, $H_3$); 8.2 (d, 1H, $H_2$, J($H_2$–$H_3$): 2.2 Hz).

EXAMPLE 44

5-Propyl-7-[(N-pyrrolidinoethyl)amino]-6-[(2'-(1H-tetrazol-5-yl)biphenyl-4-yl)methyl]pyrazolo[1,5-a]pyrimidine

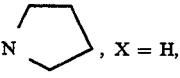

$R_2$ = n-propyl,

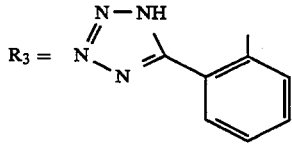

Empirical formula: $C_{29}H_{33}N_9$. Melting point: 200°–201° C. $^1$H NMR (DMSO-$d_6$): 2.6 (t, 2H, propyl $CH_2$); 6.4 (d, 1H, $H_3$); 8 (d, 1H, $H_2$, J($H_2$–$H_3$): 2 Hz).

EXAMPLE 45

7-Amino-6-[(2'-(1H-tetrazol-5-yl)biphenyl-4-yl)methyl]-5-propylpyrazolo[1,5-a]pyrimidine Formula (I): $R_1$ = $NH_2$, $R_2$ = n-propyl, X = H,

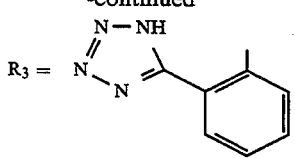

Empirical formula: $C_{23}H_{22}N_8$. Melting point: 255° C. $^1$H NMR (DMSO-$d_6$): 2.5 (m, 2H, propyl $CH_2$+DMSO-$d_6$); 6.3 (d, 1H, $H_3$); 8 (d, 1H, $H_2$, J($H_2$–$H_3$): 2 Hz).

EXAMPLE 46

7-N,N-Diethylamino-5-propyl-6-[(2,-(1H-tetrazol-5-yl)biphenyl-4-yl)methyl]pyrazolo[1,5-a]pyrimidine hydrochloride

$R_2$ = n-propyl, X = H,

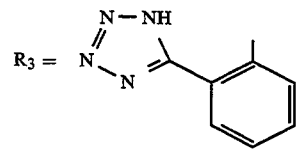

Empirical formula: $C_{27}H_{29}N_5 \cdot HCl$. Melting point: 192° C. $^1$H NMR (DMSO-$d_6$): 2.68 (t, 2H, propyl $CH_2$); 6.63 (d, 1H, $H_3$); 8.21 (d, 1H, $H_2$).

EXAMPLE 47

5-Butyl-7-hydroxy-6-[(2'-(1H-tetrazol-5-yl)biphenyl-4-yl)methyl]pyrazolo[1,5-a]pyrimidine Formula (I): $R_1$ = OH, $R_2$ = n-butyl, X = H,

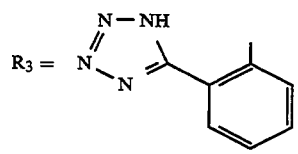

Purified by chromatography on silica gel (eluent: dichloromethane 90%/methanol 10%).

Empirical formula: $C_{24}H_{23}N_7O$. Melting point: >370° C. with decomposition. $^1$H NMR (DMSO-$d_6$): 2.51 (m, n-propyl $CH_2$/DMSO-$d_6$); 5.99 (d, 1H, $H_3$); 7.8 (d, 1H, $H_2$, J($H_2$–$H_3$): 1.8 Hz).

EXAMPLE 48

5-Propyl-6-[(2'-(1H-tetrazol-5-yl)biphenyl-4-yl)methyl]pyrazolo[1,5-a]pyrimidine Formula (I): $R_1$ = H, $R_2$ = n-propyl, X = H,

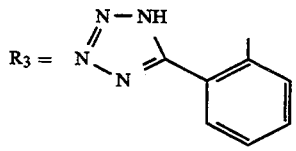

Purified by crystallization from acetonitrile.

Empirical formula: $C_{23}H_{21}N_7$. Melting point: 196° C. $^1H$ NMR (DMSO-$d_6$): 2.64 (t, 2H, n-propyl $CH_2$); 4.05 (s, 2H, benzyl $CH_2$); 6.58 (d, 1H, $H_3$); 8.11 (d, 1H, $H_2$, $J(H_2-H_3)$: 1.8 Hz); 8.89 (s, 1H, $H_7$).

EXAMPLE 49

5,7-Dipropyl-6-[(2'-(1H-tetrazol-5-yl)biphenyl-4-yl)methyl]pyrazolo[1,5-a]pyrimidine Formula (I): $R_1$ = n-propyl, $R_2$ = n-propyl, X = H

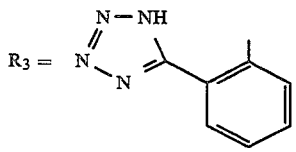

Purification by recrystallization from isopropyl acetate.

Empirical formula: $C_{26}H_{27}N_7$.

Melting point: 188° C. $^1H$ NMR (DMSO-$d_6$): 2.64 (t, 2H, n-propyl $CH_2$); 3.17 (t, 2H, n-propyl $CH_2$); 4.16 (s, 2H, benzyl $CH_2$); 6.59 (s, 1H, $H_3$); 8.13 (s, 1H, $H_2$).

EXAMPLE 50

6-[(2'-Aminocarbonylbiphenyl-4-yl)methyl]-7-hydroxy-5-propylpyrazolo[1,5-a]pyrimidine Formula (I): $R_1$ = OH, $R_2$ = n-propyl, X = H,

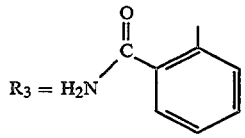

7.4 g of the compound of Example 18 in a solution of NaOH, prepared from 29.6 g of sodium hydroxide pellets and 700 ml of water, are refluxed for 3 h. The white precipitate is filtered off and treated with a dilute solution of acetic acid. Purification by recrystallization from 2-methoxyethanol gives 3.4 g of 6-[(2'-aminocarbonyl-biphenyl-4-yl)methyl]-7-hydroxy-5propylpyrazolo[1,5-a]pyrimidine.

Empirical formula: $C_{23}H_{22}N_4O_4$. Melting point: 264° C. $^1H$ NMR (DMSO-$d_6$): 2.64 (t, 2H, n-propyl $CH_2$); 3.9 (s, 2H, benzyl $CH_2$); 6.09 (d, 1H, $H_3$); 7.85 (d, 1H, $H_2$, $J(H_2-H_3)$: 1.7 Hz).

EXAMPLE 51

6-[(2'-Carboxybiphenyl-4-yl)methyl]-7-hydroxy-5-propylpyrazolo[1,5-a]pyrimidine

Formula (I): $R_1$ = OH, $R_2$ = n-propyl, X = H,

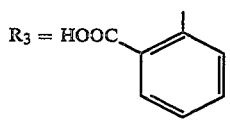

A mixture of 7.4 g of the compound of Example 18 in a solution of NaOH, prepared from 40 g of sodium hydroxide pellets and 500 ml of water, is refluxed for 6 h. The white precipitate, melting at 230°-240° C., obtained after treatment with dilute acetic acid is refluxed again for 18 h with a mixture of 6 g of NaOH, 6 ml of water and 200 ml of ethylene glycol. The resulting mixture is concentrated under vacuum and taken up in water. Treatment with a solution of acetic acid gives a precipitate which, when purified by recrystallization from 2-methoxyethanol, gives 4 g of 6-[(2'-carboxybiphenyl-4-yl)methyl]-7-hydroxy-5-propyl-pyrazolo[1,5-a]pyrimidine.

Empirical formula: $C_{23}H_{21}N_3O_3$. Melting point: 300° C. $^1H$ NMR (DMSO-$d_6$): 2.63 (t, 2H, n-propyl $CH_2$); 3.91 (s, 2H, benzyl $CH_2$); 6.09 (d, 1H, $H_3$); 7.85 (d, 1H, $H_2$, $J(H_2-H_3)$: 1.9 Hz).

PHARMACOLOGY

A · Study of the adrenal angiotensin II receptors

I. Principle

The affinity of the products of the Examples for the angiotensin II receptors is evaluated by the technique of displacing a radioligand specifically bound to rat adrenal angiotensin II receptors.

II. Procedure

An aliquot of a rat adrenal gland homogenate incubates in the presence of a single concentration of [$^{125}$I]-SIAII (Sar$^1$,Tyr$^4$,Ile$^8$-angiotensin II), which is an angiotensin II receptor antagonist, and two concentrations of competing agents ($10^{-5}$M, $10^{-7}$M) for 60 min at 25° C.

The reaction is completed by the addition of a buffer, followed by rapid filtration through glasspaper filters. The non-specific binding is determined in the presence of angiotensin II.

III. Expression of the results

The results are expressed, for the concentrations tested, as the percentage displacement of the radioligand specifically bound to the adrenal angiotensin II receptors.

IV. Results

| Product of | IV. Results % displacement of the labeled ligand | |
|---|---|---|
|  | 1E-7M | 1E-5M |
| Example 38 | 65 | 39 |
| Example 40 | 70 | 51 |
| Example 41 | 68 | 40 |
| Example 42 | 68 | 38 |
| Example 43 | 65 | 21 |
| Example 44 | 72 | 48 |
| Example 45 | 64 | 46 |
| Example 46 | 72 | 49 |

B · Measurement of the inhibition of the cell proliferation induced by a growth factor (example: Platelet-Derived Growth Factor, or PDGF) in rat aorta smooth muscle cells I. Principle The inhibition of the cell proliferation induced by a growth factor (example: PDGF) is evaluated by measuring the incorporation of $^3$H-thymidine in rat aorta smooth muscle cells (VSMC).

II. Procedure

The VSMC are cultivated at 37° C. in 5% $CO_2$ until subconfluence is reached, and are then placed for 24 hours at rest in a serum-poor medium. They are subsequently pretreated for one hour with the test molecule ($10^{-4}$M) and then stimulated for 22 hours with a growth factor (example: PDGF). $^3$H-Thymidine is incorporated during the last 4 hours. All these steps are performed at 37° C. in 5% $CO_2$.

The reaction is terminated by sucking off the reaction medium, detaching the cells and then filtering the lyzed cells through glassfiber filters.

III. Expression of the results

The results are expressed as the percentage inhibition of the stimulation of incorporation of $^3$H-thymidine due to the action of the growth factor.

Under these conditions, the tested products of formula (I) of the Examples have an antiproliferative activity at 100 μM.

TOXICOLOGY

The products of the Examples described have an excellent tolerance after oral administration.

Their 50% lethal dose in rats was found to be greater than 300 mg/kg.

CONCLUSION

The products of the Examples described have a good affinity for the angiotensin II receptors. In this respect they may be used beneficially for the various pathological conditions in which angiotensin II is involved, in particular for the treatment of arterial hypertension and cardiac insufficiency, in dosages of 1 to 400 mg by oral administration and of 0.01 to 50 mg by intravenous administration, in one or more dosage units per day. Furthermore, some of the compounds also have an antiproliferative activity and in this respect are of potential value in the treatment of proliferative diseases such as atherosclerosis.

What is claimed is:

1. A pyrazolopyrimidine compound of formula (I):

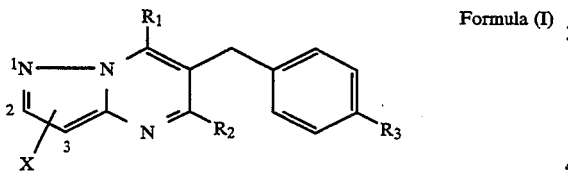

Formula (I)

in which:
one of the radicals $R_1$ and $R_2$ is
a lower alkyl radical having 1 to 6 carbon atoms; or
an ether radical of the formula —$(CH_2)_pOR$, in which p is an integer from 1 to 6 and R is a lower alkyl radical having 1 to 6 carbon atoms or a benzyl radical; and
the other radical $R_1$ or $R_2$ is
the hydrogen atom;
a halogen atom;
a lower alkyl radical having 1 to 6 carbon atoms; or
a radical selected from the group consisting of the radicals $OR_4$, $SR_4$, $NR_5R_6$ and $NH(CH_2)_n$—$NR_5R_6$,
in which:
$R_4$ is
the hydrogen atom;
a lower alkyl radical having 1 to 6 carbon atoms or a $C_3$-$C_7$-cycloalkyl radical;
a radical $(CH_2)_m$—$COOR'$, m being an integer from 1 to 4 and R' being the hydrogen atom or a lower alkyl radical having 1 to 6 carbon atoms; or
a radical $(CH_2)_m$—O—R', m and R' being as defined above;
$R_5$ and $R_6$, which are identical or different, are
the hydrogen atom; or a lower alkyl radical having 1 to 6 carbon atoms or a $C_3$-$C_7$-cycloalkyl radical; or
$R_5$ and $R_6$, taken together with the nitrogen atom to which they are attached, form a heterocycle selected from morpholine, pyrrolidine or piperidine; and
n is an integer from 1 to 4;
X, in the 2- or 3-position of the pyrazolo[1,5-a]pyrimidine ring, is
the hydrogen atom;
a lower alkyl radical having 1 to 6 carbon atoms; or
a radical selected from the group consisting of the hydroxyl radical and the radical COOR', R' being as defined above; and
$R_3$ is a radical of the formula

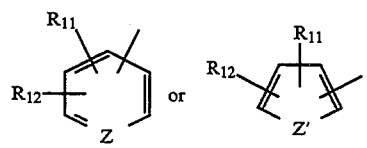

in which:
Z is CH or N; Z' is S or O;
$R_{11}$ is the hydrogen atom or a halogen atom; and
$R_{12}$ is a tetrazole radical, CN, COOH or $CONH_2$;
as well as its tautomeric forms and its pharmaceutically acceptable addition salts.

2. A compound of formula (I) according to claim 1 wherein:
one of the radicals $R_1$ and $R_2$ is
a lower alkyl radical having 1 to 6 carbon atoms; and
the other radical $R_1$ or $R_2$ is
the hydrogen atom;
a halogen atom;
a lower alkyl radical having 1 to 6 carbon atoms; or
a radical selected from the group consisting of the radicals OH, $NR_5R_6$ and $NH(CH_2)_n$—$NR_5R_6$,
in which:
$R_5$ and $R_6$, which are identical or different, are
the hydrogen atom; or
a lower alkyl radical having 1 to 6 carbon atoms; or
$R_5$ and $R_6$, taken together with the nitrogen atom to which they are attached, form a heterocycle selected from morpholine or pyrrolidine; and
n is an integer from 2 to 4;
X, in the 2- or 3-position of the pyrazolo[1,5-a]pyrimidine ring, is
the hydrogen atom; or
a lower alkyl radical having 1 to 6 carbon atoms; and
$R_3$ is one of the following radicals:

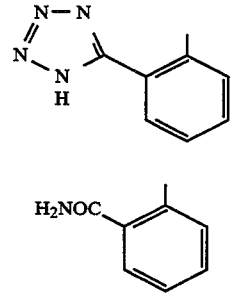

as well as its tautomeric forms and its pharmaceutically acceptable addition salts.

3. The compound according to claim 1 or claim 2 wherein $R_1$ is an n-propyl, hydroxyl, morpholinoethylamino, amino or N-diethylamino group.

4. The compound according to claim 1 or claim 2 wherein $R_2$ is an n-propyl or hydroxyl group.

5. The compound according to claim 1 or claim 2 wherein X is the hydrogen atom.

6. The compound according to claim 1 or claim 2 wherein $R_3$ is a 2-(1H-tetrazol-5-yl)phenyl group.

7. The compound according to claim 1 or claim 2 which is selected from the derivatives of the formulae 8. A pharmaceutical composition which comprises a pharmaceutically effective amount of at least one compound of formula (I) as defined in claim 1 or claim 2, or one of its pharmaceutically acceptable addition salts, incorporated in a pharmaceutically acceptable excipient, vehicle or carrier.

9. A method for the treatment of cardiovascular diseases for mammals, which comprises administering to this mammal a therapeutically effective amount of one compound of formula (I) as defined in claim 1, or one of its pharmaceutically acceptable addition salts.

10. A method for the treatment of cardiovascular diseases for mammals, which comprises administering to this mammal a therapeutically effective amount of one compound of formula (I) as defined in claim 2, or one of its pharmaceutically acceptable addition salts.

11. A pyrazolopyrimidine compound of formula (I):

Formula (I)

in which:
one of the radicals $R_2$ and $R_3$ is
a lower alkyl radical having 1 to 6 carbon atoms; or
an ether radical of the formula —$(CH_2)_m OR$, in which p is an integer from 1 to 6 and R is a lower alkyl radical having 1 to 6 carbon atoms or a benzyl radical; and
the other radical $R_1$ and $R_2$ is
the hydrogen atom;
a halogen atom;
a lower alkyl radical having 1 to 6 carbon atoms: or
a radical selected from the group consisting of the radicals $OR_4$, $SR_4$, $NR_5R_6$ and $NH(CH_2)_n$—$NR_5R_6$,
in which:
$R_4$ is
the hydrogen atom;
a lower alkyl radical having 1 to 6 carbon atoms or a $C_3$–$C_7$-cycloalkyl radical;
a radical $(CH_2)_m$—COOR', m being an integer from 1 to 4 and R' being the hydrogen atom or a lower alkyl radical having 1 to 6 carbon atoms; or a radical $(CH_2)_m$—O—R', m and R' being as defined above;

$R_5$ and $R_6$, which are identical or different, are
the hydrogen atom; or
a lower alkyl radical having 1 to 6 carbon atoms or a $C_3$–$C_7$-cycloalkyl radical; or $R_5$ and $R_6$, taken together with the nitrogen atom to which they are attached, form a heterocycle selected from morpholine, pyrrolidine or piperidine; and n is an integer from 1 to 4;

$R_3$ is a radical of the formula

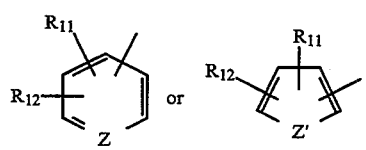

in which:
Z is CH or N; Z' is S or O;
$R_{11}$ is the hydrogen atom or a halogen atom; and
$R_{12}$ is a tetrazole radical, CN, COOH or $CONH_2$;
as well as its tautomeric forms and its pharmaceutically acceptable addition salts.

12. A compound of formula (I) according to claim 11, wherein:
one of the radicals $R_1$ and $R_2$ is
a lower alkyl radical having 1 to 6 carbon atoms; and
the other radical $R_1$ or $R_2$ is
the hydrogen atom;
a halogen atom;
a lower alkyl radical having 1 to 6 carbon atoms; or
a radical selected from the group consisting of the radicals OH, $NR_5R_6$ and $NH(CH_2)_n$—$NR_5R_6$,
in which:
$R_5$ and $R_6$, which are identical or different, are
the hydrogen atom; or
a lower alkyl radical having 1 to 6 carbon atoms; or
$R_5$ and $R_6$, taken together with the nitrogen atom to which they are attached, form a heterocycle selected from morpholine or pyrrolidine; and
n is an integer from 2 to 4:
$R_3$ is one of the following radicals:

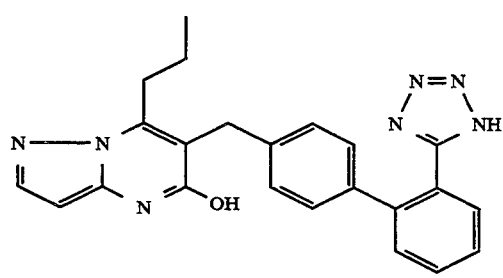

-continued

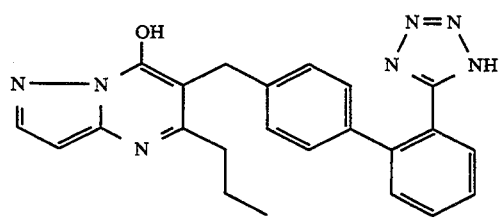

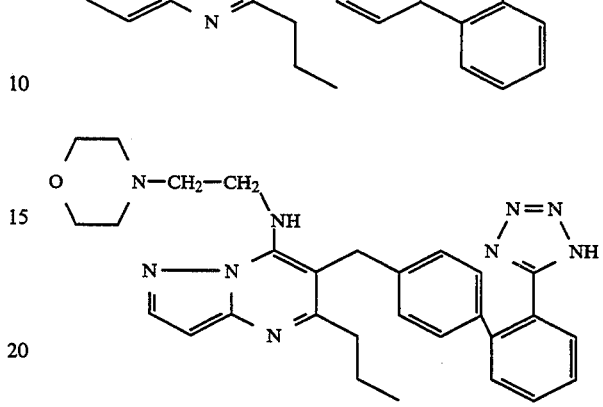

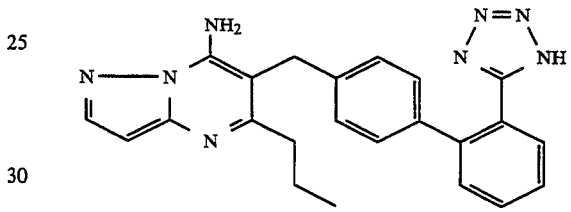

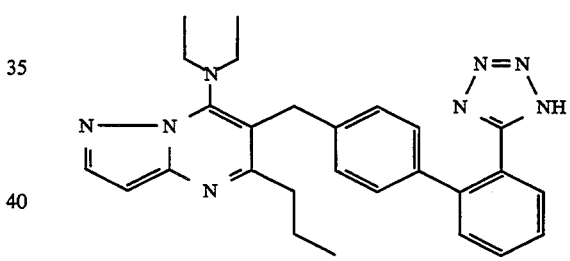

as well as its tautomeric forms and its pharmaceutically acceptable addition salts.

13. A compound according to claim 11, wherein $R_1$ is an n-propyl, hydroxyl, morpholinoethylamino, amino or N-diethylamino group.

14. A compound according to claim 11, wherein $R_2$ is an n-propyl or hydroxyl group.

15. A compound according to claim 11, wherein $R_3$ is a 2-(1H-tetrazol-5-yl) phenyl group.

16. A compound according to claim 11, which is selected from the derivatives of the formulae:

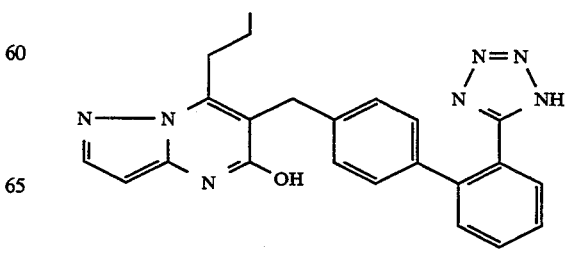

-continued
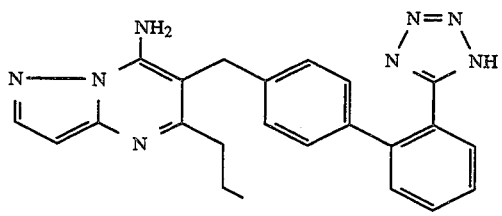
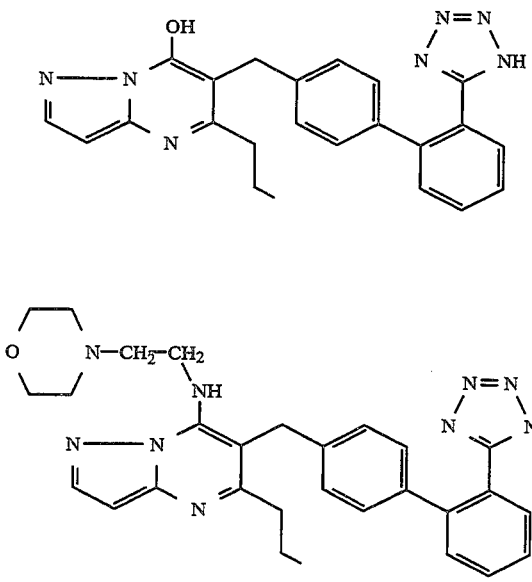
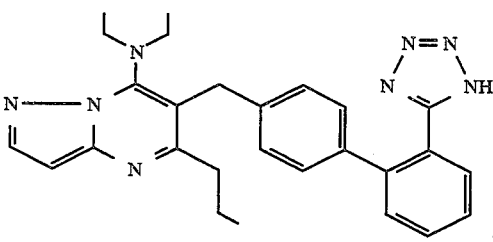
17. A pharmaceutical composition which comprises a pharmaceutically effective amount of at least one compound of formula (I) as defined in claim 11 or a pharmaceutically acceptable addition salt thereof, incorporated in a pharmaceutically acceptable excipient, vehicle or carrier.
* * * * *